United States Patent
Dao et al.

(10) Patent No.: US 12,150,919 B2
(45) Date of Patent: Nov. 26, 2024

(54) NANO LIQUID COMPOSITION CONTAINING CURCUMIN HAVE THE ABILITY TO TREATING BURNS AND INCREASING THE EFFECT OF SCAR HEALING AND METHOD OF MANUFACTURING THE SAME

(71) Applicant: Kim Dung Thi Dao, Ho Chi Minh (VN)

(72) Inventors: Kim Dung Thi Dao, Ho Chi Minh (VN); Minh Hai Luu, Ha Noi (VN)

(73) Assignee: DKD INTERNATIONAL PRODUCTION JOINT STOCK COMPANY, Ho Chi Minh (VN)

( * ) Notice: Subject to any disclaimer, the term of this patent is extended or adjusted under 35 U.S.C. 154(b) by 0 days.

(21) Appl. No.: 18/611,735

(22) Filed: Mar. 21, 2024

(65) Prior Publication Data
US 2024/0335396 A1    Oct. 10, 2024

Related U.S. Application Data

(63) Continuation-in-part of application No. 18/450,414, filed on Aug. 16, 2023.

(51) Int. Cl.
| | | |
|---|---|---|
| *A61K 31/12* | (2006.01) | |
| *A61K 9/107* | (2006.01) | |
| *A61K 31/355* | (2006.01) | |
| *A61K 31/519* | (2006.01) | |
| *A61K 36/82* | (2006.01) | |
| *A61K 36/886* | (2006.01) | |
| *A61K 47/10* | (2017.01) | |
| *A61K 47/24* | (2006.01) | |
| *A61K 47/36* | (2006.01) | |
| *A61P 17/02* | (2006.01) | |

(52) U.S. Cl.
CPC ............ *A61K 31/12* (2013.01); *A61K 9/1075* (2013.01); *A61K 31/355* (2013.01); *A61K 31/519* (2013.01); *A61K 36/82* (2013.01); *A61K 36/886* (2013.01); *A61K 47/10* (2013.01); *A61K 47/24* (2013.01); *A61K 47/36* (2013.01); *A61P 17/02* (2018.01)

(58) Field of Classification Search
None
See application file for complete search history.

*Primary Examiner* — Celeste A Roney

(57) ABSTRACT

The nano liquid composition containing curcumin have the ability to treating burns and increasing the effect of scar healing obtained by homogenously mixing a curcumin nano ingredient with a foundation mixture in a ratio of 1:1 by emulsifying equipment. The composition overcomes the disadvantages of curcumin, an organic compound with a broad spectrum of activities, including hard to dissolve in water, poor stability, and rapidly transformed. In addition, the composition of the present invention is used at a dose of 0.05-0.1 mL/cm 2 of skin, with a frequency of twice daily, had increased effect of scar healing in experimental doxorubicin-induced mouse models of skin ulceration, increased concentration of hydroxyprolin in skin, improved skin microstructure compared to control models after 21 days of application; and had no systemic toxicity after 21 days of application in the doxorubicin-induced skin ulcered mouse.

3 Claims, 10 Drawing Sheets

NANO LIQUID COMPOSITION CONTAINING CURCUMIN HAVE THE ABILITY TO TREATING BURNS AND INCREASING THE EFFECT OF SCAR HEALING AND METHOD OF MANUFACTURING THE SAME

CLAIM OF PRIORITY

This application is a continuation-in-part (CIP) application under 37 C.F.R. § 1.53(b)(2) and 35 U.S.C. § 121 of the previously filed application Ser. No. 18/450,414, entitled, "Nano liquid composition containing curcumin have the ability to treating burns and increasing the effect of scar healing and method of manufacturing the same", by Kim Dung Thi Dao; which, in turn, claims priority under 35 U.S.C. § 119 of an application No. 1-2023-02270 filed on Apr. 5, 2023 in the Socialist Republic of Vietnam.

FIELD OF THE INVENTION

In various aspects, the invention relates to immunological therapies for treating a condition characterized by inflammation. In alternative embodiments, the invention provides nano liquid composition containing curcumin have the ability to treating burns and increasing the effect of scar healing and method of manufacturing the same.

BACKGROUND ART

In recent years, along with the trend of returning to using natural products, the development of active herbal ingredients has become an increasingly important concern for the pharmaceutical industry in Vietnam. In which, the group of curcuminoid pigments extracted from the rhizomes of yellow turmeric (*Curcuma longa* L.) has attracted the attention of scientists because of its significant biological effects. Curcumin is the main component found in the rhizome of Turmeric, in addition to other curcuminoids, for example, demethoxycurcumin, bisdemethoxycurcumin.

Curcumin is a natural compound isolated from Turmeric *Curcuma longa* L. (ginger family—Zingiberaceae), scientific name is (1E,6E)1,7-bis (4'-hydroxy-3'-metoxyphenyl)-1,6-heptadiene-3,5-dion (English: (1E,6E)-1,7-bis(4-hydroxy-3'-methoxyphenyl)-1,6-heptadiene-3,5-dione), in the structure Molecular structure with 1,3-dicetone group (β-dicetone) can participate in ketone-enol conversion.

Curcumin is practically insoluble in water at acidic and neutral pH (<0.1 µg/mL) and soluble in alkali. Curcumin is soluble in water in the presence of surfactants such as sodium dodecyl sulfate, cetyl pyridine bromide, gelatin, polysaccharides, polyethylene glycol, and cyclodextrin. Curcumin is soluble in acetic acid, ethanol, methanol, acetone, dimethyl sulfoxide, dichloromethane, chloroform, ethyl acetate, acetonitrile; slightly soluble in n-hexane, and cyclohexane; insoluble in ether.

Electrolysis according to the pH of curcumin, an aqueous solution of curcumin ($H_3A$) exists in many different ionic forms depending on the pH. At a pH<1, the solution, the aqueous form of curcumin ($H_3A$), is red in color and exists in the form of H4A+ ions. At pH=1-7, curcumin is very slightly soluble in water, and aqueous solutions of curcumin at this pH range are yellow and exist mainly in the neutral $H_3A$ form. At pH >7.5, the aqueous solution of curcumin is red; curcumin exists in the ionic forms $H_2A^-$, $HA^{2-}$, and $A^{3-}$, corresponding to pka values of 7.8, 8.5, and 9.0.

In addition, chemically, curcumin contains the functional groups —OH phenol, β-diacetone, alkenes, and aromatic nucleus, so curcumin has characteristic chemical reactions of these functional groups, including, for example, hydrogenation, iminization, and complexation with metal ions.

Under the effect of light, curcumin decomposes into vanillin, vanillic acid, ferulic aldehyde, and ferulic acid. Curcumin is also unstable in the presence and absence of oxygen. In the presence of oxygen and light, curcumin decomposes from 4-vinylguaialcol and vanillin. In the lack of oxygen, curcumin can undergo intramolecular cyclization to form condensation products.

Curcumin has been studied and proven to have pharmacological effects including, but not limited to anti-inflammatory, antioxidant, antibacterial, antiviral, anticancer, wound healing, and scar healing.

Specifically, curcumin is considered the most representative substance for a new generation of anti-cancer agents that are both very effective and safe without causing side effects. This compound is the most potent cytotoxic substance by the mechanism of killing malignant cells, inactivating cancer cells, and preventing the formation of new cancer cells without affecting other cells. Adjacent benign cells. Meanwhile, many drugs, when killing malignant cells, also kill healthy cells, making the body exhausted.

Curcumin also has the powerful ability to detoxify and protect liver cells, protect and increase red blood cells, remove LDL cholesterol, regulate blood pressure, lower blood cholesterol, prevent obesity, and remove freckles and age spots. Acne, prevent hair loss, help hair grow quickly, make skin ruddy, etc.

Curcumin is also one of the typical anti-inflammatory and antioxidant substances. It supports the treatment of cancer, gastric ulcer, duodenal bulb, colon, Parkinson's disease, and cerebral palsy. Curcumin is highly effective for immune system disorders such as systemic inflammation, polyarthritis, periarthritis, uveitis, multiple sclerosis, and ankylosing spondylitis. Scleroderma, osteoporosis, myasthenia gravis, psoriasis, systemic lupus erythematosus, polymyositis, multiple gastrointestinal granulomas, thyroid disorders, hemangiomas, bleeding, hemophilia, melanoma, memory loss, memory loss.

Acute wounds usually heal in an orderly manner and progress smoothly through four stages: hemostasis (haemostasis), inflammation (inflammation), proliferation (proliferation), and remodeling (remodelling). In contrast, chronic wounds also initiate the healing process, but prolonged periods of inflammation, proliferation, or regeneration lead to tissue fibrosis and non-healing ulcers. Wound healing is complex and involves many types of differentiated cells, such as platelets, macrophages, fibroblasts, epithelial cells, and endothelial cells. These cells interact with each other and with the extracellular matrix. In addition to the various intercellular effects, wound healing is also influenced by the activity of proteins and glycoproteins such as cytokines, chemokines, growth factors, inhibitors, and their receptors. Each phase of wound healing has certain milestones that must occur for normal wound healing to occur.

A burn is a type of injury to the skin or other tissues caused by heat, electricity, chemicals, friction, or radiation. Most burns are caused by hot heat from liquids, solids, or combustibles.

Most cotton is preventable. Treatment depends on the severity of the burn. Burns were classified according to depth (thick superficial burns and deep localized thick burns, complete thick burns) and percentage of burns to total body surface area (TBSA). Complications and problems include hypovolemic shock, aspiration injury, infection, scarring, and spasms. Patients with extensive burns (>20% TBSA) require fluid resuscitation.

Burns cause both systemic and local complications. The main factors contributing to systemic complications are skin tearing and fluid loss. Local complications include scab scarring, spasticity, and scarring.

Systemic Burn Complications of

The greater the percentage of burns to body surface area (TBSA), the greater the risk of developing systemic complications. Risk factors for serious and fatal systemic complications include all of the following:

Second-degree and third-degree burns=40% TBSA
Age >60 years old or <2 years old
Concurrent major trauma or smoke inhalation The most common systemic complications of systemic burns are hypovolemia and infection. Volume depletion, which causes hypoperfusion of burned tissue and sometimes shock, may be due to fluid loss from deep sloughs or is associated with large surface burn areas; Generalized edema due to loss of intravascular fluid to interstitial tissue and cells.

In addition, complications can result in metabolic abnormalities that may include hypoalbuminemia, partly due to hemodilution (secondary to fluid replacement) and partly due to loss of protein in the compartment extra vascularity through damaged capillaries. Dilution electrolyte deficiencies may develop; These include decreased magnesium, decreased phosphorus, and decreased potassium. Metabolic acidosis can be the result of shock. Rhabdomyolysis or hemolysis can result from deep thermal burns or electrical burns to the muscle due to ischemia leading to spasticity. Myoglobinuria-induced rhabdomyolysis or hemoglobinuria-induced hemolysis can lead to acute tubular necrosis and acute kidney injury.

Local Burn Complications

Scaly scars, dead tissue from deep burns. A round, scaly scar that completely encloses a limb (or sometimes the neck or trunk), potentially with spasm. A constrictive squamous scar limits tissue expansion in response to edema; instead, the tissue increases pressure, eventually causing ischemia. The ischemia threatens the viability of the extremities, and the distance to the squamous scar, a scab around the neck or thorax, can impair ventilation.

Scarring and spasticity result from the healing of deep burns. Depending on the extent of the scar, spastic deformity may occur in the joints. If the burn is located near a joint (especially on the hands), on the feet, or on the perineum, a function may be severely impaired. Infection can increase scarring. Fault scars form in some burn patients, especially in darker-skinned patients.

Skin Ulcers

Skin ulcers are sores on the skin or mucous membrane, accompanied by tissue disintegration. Ulcers can lead to complete loss of the epidermis and often part of the hypodermis and even subcutaneous fat. Ulcers are most common on the skin of the lower extremities and in the gastrointestinal tract. An ulcer that appears on the skin is usually visible as an inflamed tissue with an area of red skin. A skin sore is usually visible in case of exposure to heat or cold, irritation, or problems with blood circulation. They can also be caused by a lack of mobility, which causes prolonged pressure on the tissues. This tension in blood circulation is converted into skin ulcers, commonly known as bed sores or recumbent ulcers. Ulcers often become infected and form pus. Skin ulcers can progress very quickly, especially in people who are weak resistance.

Ulcers develop in stages. In the first stage, the skin is red with soft tissue underneath. In the second stage, the redness of the skin becomes more pronounced, swelling appears, and there may be some blisters and loss of the outer layer of skin. In the next stage, the skin may be necrotic down through the deep layers of the skin, and the fat underneath the skin may be exposed and visible. In the fourth stage, deeper necrosis often occurs, the fat beneath the skin is completely exposed, and the muscle may also be exposed. In the last two stages, pain can cause more fat loss and muscle necrosis; In severe cases, it can go all the way to the bone, bone destruction can begin, and there may be a joint infection.

The wound healing effect of curcumin. Curcumin is the main component of yellow turmeric extract with antioxidant, remove free radical scavenging, antibacterial, and anti-inflammatory effects that play an important role in the wound healing process. Furthermore, curcumin has the ability to stimulate the production of growth factors involved in wound healing; therefore, curcumin has the effect of speeding up and accelerating wound healing and healing.

For the inflammatory phase, several studies have shown that curcumin reduces the expression of inflammatory cytokines such as tumor necrosis factor-alpha (TNF-$\alpha$) and interleukin-1 (IL-1). Curcumin also inhibits NF-KB, which is a stimulus factor in inflammatory pathways. The anti-inflammatory effects of curcumin are also associated with other signaling pathways, including the PPAR-y receptor-stimulating signaling pathway (a gamma receptor activated by peroxisomal proliferators) and the TLR4-MD2 co-receptor. (myeloid-differentiated 2-TLR4 protein co-receptor).

As described above, although curcumin has many important effects, however, it has disadvantages such as difficulty in water solubility, poor stability, and rapid metabolism when used orally; therefore, the bioavailability of curcumin is low. On the other hand, curcumin is yellow and difficult to wash off, so the need for curcumin is limited, especially in cosmetics. With the limitations of curcumin, the use of curcumin in preparations, topical products, and cosmetics has also been gradually replaced by tetrahydrocurcumin derivatives, a substance sold synthetically from curcumin. Colorless tetrahydrocurcumin should be used more widely; moreover, studies also show that tetrahydrocurcumin has better antioxidant, anti-inflammatory and anti-cancer effects than curcumin. Tetrahydrocurcumin is considered to be the final metabolite of curcumin in the body, so using tetrahydrocurcumin instead can overcome the disadvantage of curcumin's poor bioavailability.

Nanoization of bioactive compounds is a rapidly expanding branch of the food, pharmaceutical, and/or preparation industries that, in addition to protecting bioactive compounds, improves bioavailability. Chemistry, solubility, permeability, absorption, etc. Since the application of bioactive compounds is mostly limited due to problems such as low solubility, instability, uncontrolled release, and low bioavailability, many studies have been conducted on the distribution system of these valuable compounds. Among the different types of nanosystems, it is better to choose a nanosystem that allows to overcome the above disadvantages of the active ingredient, more stability, compatibility, and lower toxicity.

Silver sulfadiazine is an antibacterial drug synthesized from the reaction of silver nitrate with sulfadiazine that is used topically for the prevention and treatment of infections in second- and third-degree burns. The mechanism of action of silver sulfadiazine is different from silver nitrate and sulfadiazine. Silver sulfadiazine acts on the membrane and envelope (wall) of bacterial cells.

Silver sulfadiazine itself is not absorbed. When in contact with tissues and body fluids, silver sulfadiazine reacts slowly with sodium chloride, sulfhydryl groups, and proteins to release sulfadiazine, which can be absorbed into the body from the site of application, especially when applied topically. 2nd-degree burns.

Care should be taken when using the drug in people with liver and kidney damage because sulfadiazine can be accumulated in the body; when treating extensive burns, serum sulfadiazine levels, and renal function should be monitored. Sulfonamide crystals must be found in the urine, and when silver sulfadiazine is used in people with enzyme glucose-6-phosphate dehydrogenase deficiency, it can cause hemolytic anemia, adverse reactions due to the absorption of sulfadiazine into the body, as reported. Silver skin infection, when used through many 1% silver sulfadiazine creams to treat wide sores, has common side effects such as itching, pain, and burning sensation.

For the treatment and healing of ulcers, dimethyl sulfoxide (Dimethyl sulfoxide—DMSO) is mainly used for pain relief and rapid healing of wounds, burns, and skin diseases. However, when DMSO is taken orally or applied to the skin, the compound causes a number of side effects, including skin reactions, dry skin, headache, dizziness, drowsiness, nausea, vomiting, diarrhea, and constipation, breathing problems, blood problems, and allergic reactions. DMSO also causes garlic breath and body odor.

The present invention provides a solution for treating burns and increasing the healing effect of effective ulcers from organic compounds of natural origin, namely nano-preparations containing curcumin which have therapeutic effects. Treats burn and increase the healing effect of ulcers better than the control (untreated) sample and are equivalent to 1% silver sulfadiazine (Sulfadiazine silver) and dimethyl sulfoxide for scar healing. (Dimethyl sulfoxide—DMSO) but does not cause systemic toxicity or adverse side effects of 1% silver sulfadiazine and DMSO, such as monitoring of serum sulfadiazine concentration and renal function; caution when using Use the drug for people with deficiency of the enzyme glucose-6 phosphate dehydrogenase because it can cause hemolytic anemia, adverse reactions due to the absorption of sulfadiazine into the body such as reported silver skin when using too much silver sulfadiazine cream 1% for the treatment of extensive ulcers, side effects and/or skin reactions, and allergic reactions commonly associated with the use of DMSO.

The invention provides solutions to achieve the above objectives.

SUMMARY OF THE INVENTION

Accordingly, an objective of the present invention is to provide a nano liquid composition containing curcumin have the ability to treating burns and increasing the effect of scar healing obtained by homogenously mixing a curcumin nano ingredient with a foundation mixture in a ratio of 1:1 for 4 hours at 120° C. by emulsifying equipment;
- wherein the foundation mixture is a phospholipid ingredient; and
- wherein the composition is used at a dose of 0.05-0.1 mL/cm$^2$ of skin, with a frequency of twice daily to reduce the area of the burns, and increasing the concentration of hydroxyproline in the skin.

Another objective of the present invention is to provide a nano liquid composition containing curcumin have the ability to treating burns and increasing the effect of scar healing obtained by homogenously mixing a curcumin nano ingredient with a foundation mixture in a ratio of 1:1 for 4 hours by emulsifying equipment;
- wherein the foundation mixture comprising phosphatidylcholine, cholesterol, lecithine, folic acid, the curcumin nano ingredient, tocopherol, and xanthan gum;
- wherein the composition is used at a dose of 0.05-0.1 mL/cm$^2$ of skin, with a frequency of twice daily to reduce the area of the burns, and increasing the concentration of hydroxyproline in the skin.

Yet another objective of the present invention is to provide a curcumin nano ingredient is obtained by performed in a specific order from (i) to (v) comprising:
- (i) preparing a dispersed phase by dissolving 4 parts of a curcumin with 5 parts of ethanol;
- (ii) creating a carrier mixture by homogeneous dissolving 1.5 parts PEG (polyethylene glycol) with 6 parts EG (ethylene glycol) and 2 parts water, with the combination of ultrasonic vibration for 2 hours at room temperature;
- (iii) creating a homogeneous mixture by homogeneous dissolving 1.6 parts of the dispersed phase at step (i) with 1.5 parts of the carrier mixture at step (ii), and 2 parts lecithin by emulsifying equipment;
- (iv) keeping the homogeneous mixture overnight; and
- (v) centrifuging said homogenized mixture at step (iv) with a speed of 5000 rpm for 10 min, and repeated 6 times of centrifugation to obtain the curcumin nano ingredient form microemulsion.

In view of the foregoing, another objective of the present invention is to provide a foundation mixture by homogenously mixing the following ingredients:
phosphatidylcholine having 15%-20% by weight;
cholesterol having 18%-25% by weight;
lecithine having 25%-30% by weight;
folic acid having 8%-12% by weight;
curcumin nano ingredient having 12%-20% by weight;
tocopherol having 2%-5% by weight;
xanthan gum having 2%-5% by weight;
*Camellia sinensis* extracts ingredient having 2%-5% by weight; and
aloe vera extracts ingredient having 0.25%-1% by weight.

Another objective of the present invention is to provide the foundation mixture comprising:
phosphatidylcholine having 18% by weight;
cholesterol having 21% by weight;
lecithine having 27% by weight;
folic acid having 9.5% by weight;
curcumin nano ingredient having 15% by weight;
tocopherol having 3% by weight;
xanthan gum having 3% by weight;
*Camellia sinensis* extracts ingredient having 3% by weight; and
aloe vera extracts ingredient having 0.5% by weight.

Finally, the purpose of the invention is to provide a method of manufacturing the nano liquid composition containing curcumin have the ability to treating burns and increasing the effect of scar healing comprising steps performed in the following specific order:
- (a) creating a curcumin nano ingredient by performed in a specific order from (i) to (v) comprising:
  - (i) preparing a dispersed phase by dissolving 4 parts of a curcumin with 5 parts of ethanol;
  - (ii) creating a carrier mixture by homogeneous dissolving 1.5 parts PEG (polyethylene glycol) with 6 parts EG (ethylene glycol) and 2 parts water, with the combination of ultrasonic vibration for 2 hours at room temperature;
(iii) creating a homogeneous mixture by homogeneous dissolving 1.6 parts of the dispersed phase at step (i) with 1.5 parts of the carrier mixture at step (ii), and 2 parts lecithin by emulsifying equipment;
(iv) keeping the homogeneous mixture overnight; and
(v) centrifuging said homogenized mixture at step (iv) with a speed of 5000 rpm for 10 min, and repeated 6 times of centrifugation to obtain the curcumin nano ingredient form microemulsion;
(b) creating a foundation mixture by homogenously mixing the following ingredients:
a phosphatidylcholine having 15%-20% by weight;
a cholesterol having 18%-25% by weight;
a lecithine having 25%-30% by weight;
a folic acid having 8%-12% by weight;
the curcumin nano ingredient having 12%-20% by weight;
a tocopherol having 2%-5% by weight;
a xanthan gum having 2%-5% by weight;
a *Camellia sinensis* extracts ingredient having 2%-5% by weight; and
an aloe vera extracts ingredient having 0.25%-1% by weight;
(c) homogenously mixing the curcumin nano ingredient at step (a) with the foundation mixture at step (b) in a ratio of 1:1 for 2 hours at 120° C. by emulsifying equipment to create a nano liquid composition containing curcumin have the ability to treating burns and increasing the effect of scar healing.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE INVENTION

Figure 1:
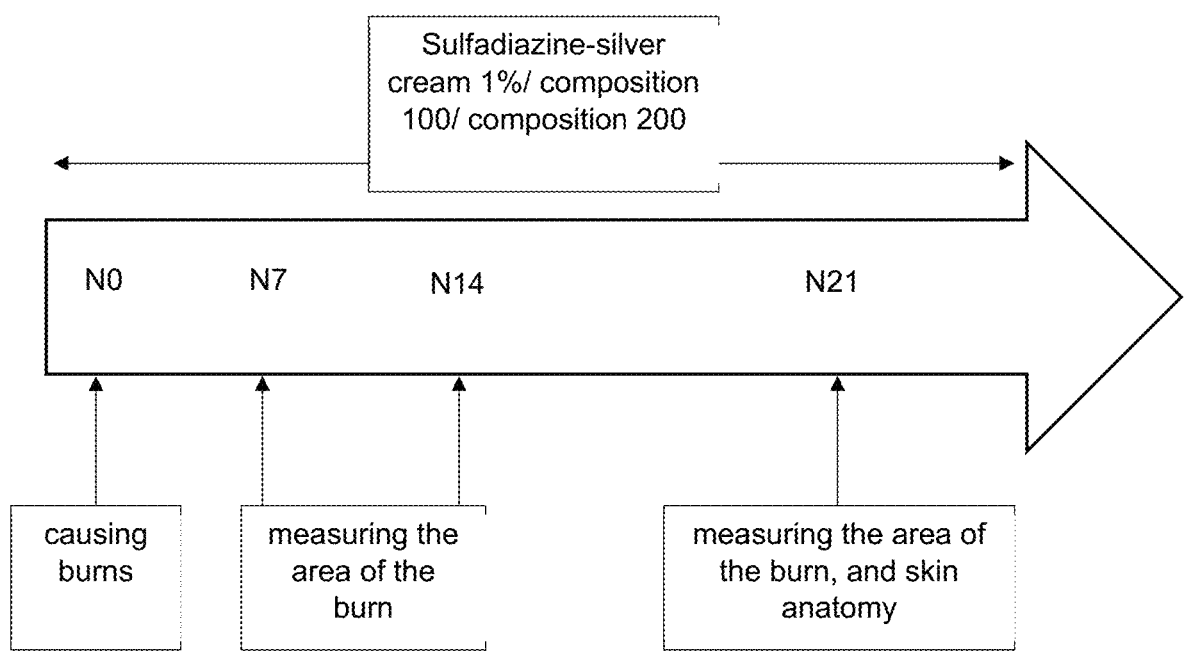
FIG. 1 is a diagram to study the effect of burn treatment on burn models on white rat skin.

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

In the embodiment of the present invention, percent mass or percentage (%) by weight=(mass of solute/mass of solution)×100%. The unit of mass is usually grams. Mass percent is also known as the correct percentage by weight or w/w %. It should also be noted that the molar mass is also within the meaning of the invention. Molar mass is the total mass of all atoms in a mole of compound. Total all volume percentages add up to 100%.

According to the embodiment of the present invention, a nano liquid composition containing curcumin have the ability to treating burns and increasing the effect of scar healing 100 ("composition 100") obtained by homogenously mixing a curcumin nano ingredient with a foundation mixture in a ratio of 1:1 for 4 hours at 120° C. by emulsifying equipment; wherein the foundation mixture is a phospholipid ingredient. It should be noted that the emulsifying equipment has been known in previous art so the description of the structure and its operating principle will not be described in detail in the invention.

It should be noted that homogenization in the embodiment of the present invention is also understood as homogenously mixing. Homogenization is the mixing of insoluble ingredients, or difficult to dissolve together, or not react to each other. In the process of homogenization, the ingredients in the resulting mixture have micro molecular sizes, evenly distributed and reduced layering effects, causing sedimentation of gravity to create the required homogenously solution.

According to the embodiment of the present invention, the curcumin nano ingredient is obtained by performed in a specific order from (i) to (v) comprising:

(i) preparing a dispersed phase by dissolving 4 parts of a curcumin with 5 parts of ethanol;

(ii) creating a carrier mixture by homogeneous dissolving 1.5 parts PEG (polyethylene glycol) with 6 parts EG (ethylene glycol) and 2 parts water, with the combination of ultrasonic vibration for 2 hours at room temperature;
(iii) creating a homogeneous mixture by homogeneous dissolving 1.6 parts of the dispersed phase at step (i) with 1.5 parts of the carrier mixture at step (ii), and 2 parts lecithin by emulsifying equipment;
(iv) keeping the homogeneous mixture overnight; and
(v) centrifuging said homogenized mixture at step (iv) with a speed of 5000 rpm for 10 min, and repeated 6 times of centrifugation to obtain the curcumin nano ingredient form microemulsion.

According to the embodiment of the present invention, curcumin is extracted from yellow turmeric (*Curcuma longa* L.). Extraction methods to obtain curcumin compounds from yellow turmeric are common in this field. Although there is no limitation on curcumin extracted from yellow turmeric, it is nevertheless preferable to use curcumin extracted from yellow turmeric according preferred embodiments of the present invention, including curcumin of at least 90% purity, preferably curcumin of at least 95% purity.

It should be noted that the term "room temperature" is used to refer to the temperature in ambient conditions which is usually between 25° C.-37° C., preferably 30° C.

In addition, it should be noted that the curcumin nano ingredient form microemulsion has a pH of 7.2. With this pH value, the particles are stable because the medium is neutral, so the bond between curumin and the carrier will be stable during dispersion.

The curcumin nano ingredient form microemulsion having a hydrophilic equilibrium (HLB) parameter of 15, which is typical for an oil/water emulsion system. This microemulsion system contains hydrophilic curcumin particles (overcoming the solubility disadvantage), non-binding (avoiding, or minimizing agglomeration), stable curcumin particle sizes in the range of 40-50 nm, so it easily penetrates through the cell membrane, thereby increasing the activity of curcumin.

The UV-vis spectroscopy method also identified that the peak positions of raw curcumin and the curcumin nano ingredient form microemulsion are completely coincidental. This shows that the curcumin nano ingredient form microemulsion obtained by the above process still retains the stable structure, and curcumin activity during the nano-chemical process. The results also show that the concentration of curcumin in the curcumin nano ingredient form microemulsion is 15%-20%.

According to the embodiment of the present invention, composition 100 is used to treat burns, reduce the area of the burn, increase the concentration of hydroxyproline in the skin, and increase the healing effect of ulcers. In addition, increasing the concentration of hydroxyproline also has a moisturizing effect on the skin because hydroxyproline has the ability to bind to water molecules and hold them for a long time.

It should be noted that hydroxyproline is an amino acid. It is a product of the hydroxylation of proline, an amino acid involved in protein molecular structure found mainly in collagen molecules, that is a characteristic fibrous material found mainly in the dermis of the skin, having a lifting effect, and creates firmness for the skin.

According to another embodiment of the invention, a nano liquid composition containing curcumin have the ability to treating burns and increasing the effect of scar healing 200 ("composition 200") obtained by homogenously mixing a curcumin nano ingredient with a foundation mixture in a ratio of 1:1 for 2 hours by emulsifying equipment; wherein the foundation mixture comprising phosphatidylcholine, cholesterol, lecithine, folic acid, nanocurumin, tocopherol, and xanthan gum.

According to the embodiment of the present invention, the nanocurumin of the foundation mixture used is the curcumin nano ingredient form microemulsion.

According to the embodiment of the invention, the foundation mixture further comprising a *Camellia sinensis* extracts ingredient.

According to the embodiment of the invention, the foundation mixture further comprising an aloe vera extracts ingredient.

According to the embodiment of the invention, the foundation mixture comprising: phosphatidylcholine having 15%-20% by weight; cholesterol having 18%-25% by weight; lecithine having 25%-30% by weight; folic acid having 8%-12% by weight; curcumin nano ingredient having 12%-20% by weight; tocopherol having 2%-5% by weight; and xanthan gum having 2%-5% by weight, the *Camellia sinensis* extracts ingredient having 2%-5% by weight, and the aloe vera extracts ingredient having 0.25%-1% by weight.

According to the preferred embodiment of the invention, the foundation mixture comprising: phosphatidylcholine having 18% by weight; cholesterol having 21% by weight; lecithine having 27% by weight; folic acid having 9.5% by weight; curcumin nano ingredient having 15% by weight; tocopherol having 3% by weight; xanthan gum having 3% by weight; *Camellia sinensis* extracts ingredient having 3% by weight; and aloe vera extracts ingredient having 0.5% by weight.

It should be noted that there are no restrictions on the mixed ingredients to create the foundation mixture as described above. The mixed ingredients are chemicals that all common to the average person in the field, therefore detailed descriptions are omitted to simplify understanding of the invention. Under some embodiments, these chemicals and materials can be procured and used in their original form from commercially available source suppliers. In some other embodiments, they can be used as-is after synthesis and/or extraction with or without further purification, arbitrarily desired.

According to the preferred embodiment of the invention, the composition 200 containing the curcumin nano ingredient obtained by performed in a specific order from (i) to (v) comprising:
(i) preparing a dispersed phase by dissolving 4 parts of a curcumin with 5 parts of ethanol; wherein the curcumin of at least 95% purity;
(ii) creating a carrier mixture by homogeneous dissolving 1.5 parts PEG (polyethylene glycol) with 6 parts EG (ethylene glycol) and 2 parts water, with the combination of ultrasonic vibration for 2 hours at room temperature;
(iii) creating a homogeneous mixture by homogeneous dissolving 1.6 parts of the dispersed phase at step (i) with 1.5 parts of the carrier mixture at step (ii), and 2 parts lecithin by emulsifying equipment;
(iv) keeping the homogeneous mixture overnight; and
(v) centrifuging said homogenized mixture at step (iv) with a speed of 5000 rpm for 10 min, and repeated 6 times of centrifugation to obtain the curcumin nano ingredient form microemulsion.

According to the embodiment of the invention, a method of manufacturing the nano liquid composition containing curcumin have the ability to treating burns and increasing the effect of scar healing 300 ("method 300") comprising steps performed in the following specific order:
(a) creating a curcumin nano ingredient by performed in a specific order from (i) to (v) comprising:
(i) preparing a dispersed phase by dissolving 4 parts of a curcumin with 5 parts of ethanol;
(ii) creating a carrier mixture by homogeneous dissolving 1.5 parts PEG (polyethylene glycol) with 6 parts EG (ethylene glycol) and 2 parts water, with the combination of ultrasonic vibration for 2 hours at room temperature;
(iii) creating a homogeneous mixture by homogeneous dissolving 1.6 parts of the dispersed phase at step (i) with 1.5 parts of the carrier mixture at step (ii), and 2 parts lecithin by emulsifying equipment;
(iv) keeping the homogeneous mixture overnight; and
(v) centrifuging said homogenized mixture at step (iv) with a speed of 5000 rpm for 10 min, and repeated 6 times of centrifugation to obtain the curcumin nano ingredient form microemulsion;
(b) creating a foundation mixture by homogenously mixing the following ingredients:
phosphatidylcholine having 15%-20% by weight;
cholesterol having 18%-25% by weight;
lecithine having 25%-30% by weight;
folic acid having 8%-12% by weight;
curcumin nano ingredient having 12%-20% by weight;
tocopherol having 2%-5% by weight;
xanthan gum having 2%-5% by weight;
*Camellia sinensis* extracts ingredient having 2%-5% by weight; and
aloe vera extracts ingredient having 0.25%-1% by weight;
(c) homogenously mixing the curcumin nano ingredient at step (a) with the foundation mixture at step (b) in a ratio of 1:1 for 2 hours at 120° C. by emulsifying equipment to create a nano liquid composition containing curcumin have the ability to treating burns and increasing the effect of scar healing.

According to the embodiment of the invention, at step (b), the foundation mixture comprising: phosphatidylcholine having 18% by weight; cholesterol having 21% by weight; lecithine having 27% by weight; folic acid having 9.5% by weight; curcumin nano ingredient having 15% by weight; tocopherol having 3% by weight; xanthan gum having 3% by weight; *Camellia sinensis* extracts ingredient having 3% by weight; and aloe vera extracts ingredient having 0.5% by weight.

The curcumin nano ingredient form microemulsion obtained obtained from method 300, the composition 100, and the composition 200 according to the present invention are used at a dose of 0.05-0.1 mL/cm$^2$ of skin, with a frequency of twice daily to reduce the area of the burns, and increasing the concentration of hydroxyproline in the skin.

The example is made according to the embodiment of the present invention. Example 1: the composition 100 obtained by homogenously mixing the curcumin nano ingredient with the phospholipid ingredient in a ratio of 1:1 for 4 hours at 120° C. by emulsifying equipment;
wherein the curcumin nano ingredient is obtained by performed in a specific order from (i) to (v) comprising:
(i) preparing a dispersed phase by dissolving 32 g curcumin with 40 mL ethanol solution 96%, with the combination of stirring 400 rpm at 40° C. for 6 hours;
(ii) creating a carrier mixture by homogeneous dissolving 30 g PEG 1000 with 120 mL EG and 40 mL water, with the combination of ultrasonic vibration for 2 hours at room temperature;
(iii) creating a homogeneous mixture by homogeneous dissolving the dispersed phase at step (i) with the carrier mixture at step (ii), and 40 mL lecithin by emulsifying equipment, with the combination of stirring 600 rpm at 80° C. for 3 hours, and then with the combination of stirring 800 rpm at 190° C. for 3 hours;
(iv) keeping the homogeneous mixture overnight; and
(v) centrifuging said homogenized mixture at step (iv) with a speed of 5000 rpm for 10 min, and repeated 6 times of centrifugation to obtain the curcumin nano ingredient form microemulsion.

Another example is made according to the embodiment of the present invention. Example 2: The composition 200 obtained by homogenously mixing the curcumin nano ingredient with the foundation mixture in a ratio of 1:1 for 2 hours at 120° C. by emulsifying equipment;
wherein the curcumin nano ingredient is obtained by performed in a specific order from (i) to (v) comprising:
(i) preparing a dispersed phase by dissolving 32 g curcumin with 40 mL ethanol solution 96%, with the combination of stirring 400 rpm at 40° C. for 6 hours;
(ii) creating a carrier mixture by homogeneous dissolving 30 g PEG 1000 with 120 mL EG and 40 mL water, with the combination of ultrasonic vibration for 2 hours at room temperature;
(iii) creating a homogeneous mixture by homogeneous dissolving the dispersed phase at step (i) with the carrier mixture at step (ii), and 40 mL lecithin by emulsifying equipment, with the combination of stirring 600 rpm at 80° C. for 3 hours, and then with the combination of stirring 800 rpm at 190° C. for 3 hours;
(iv) keeping the homogeneous mixture overnight; and
(v) centrifuging said homogenized mixture at step (iv) with a speed of 5000 rpm for 10 min, and repeated 6 times of centrifugation to obtain the curcumin nano ingredient form microemulsion;
wherein 100 g the foundation mixture by homogenously mixing the following ingredients: 18 g phosphatidylcholine, 21 g cholesterol, 27 g lecithine, 9.5 g folic acid, 15 g nanocurumin, 3 g tocopherol, 3 g xanthan gum, 3 g the *Camellia sinensis* extracts ingredient, and 0.5 g the aloe vera extracts ingredient.

Conducting a characteristic survey of treating burns for composition 100 and composition 200 compared with control samples (sulfadiazine-silver cream 1% type 20 g manufactured by Satyam Pharm & Chemicals Pvt., Ltd—India). The model was based on previous studies of thermal burns on the skin of white rats of Wistar strain, both breeds, healthy, weighing 180±20 g. Experimental animals were housed 7 days before the study and throughout the study period under laboratory conditions with adequate food and water. White rats of both breeds were randomly divided into 5 lots, each batch of 10 animals as follows:
Lot 1: No burns, no applying Sulfadiazine-silver cream 1%/composition 100/composition 200;
Lot 2: Causing thermal burns on the skin, no applying Sulfadiazine-silver cream 1%/composition 100/composition 200;
Lot 3: Causing thermal burns on the skin, applying Sulfadiazine-silver cream 1% with dose of 0.3 g/burn/time, with a frequency of twice daily;

Lot 4: Causing thermal burns on the skin, applying composition 100 with dose 0.3 ml/burn/time, with a frequency of twice daily; and Lot 5: Causing thermal burns on the skin, applying composition 200 with 0.3 ml/burn/time, 2 times/day;

wherein said Sulfadiazine-silver cream 1%, composition 100, and composition 200 were used immediately after inducing burn models on rat skin (referenced by FIG. 1).

Figure 2:
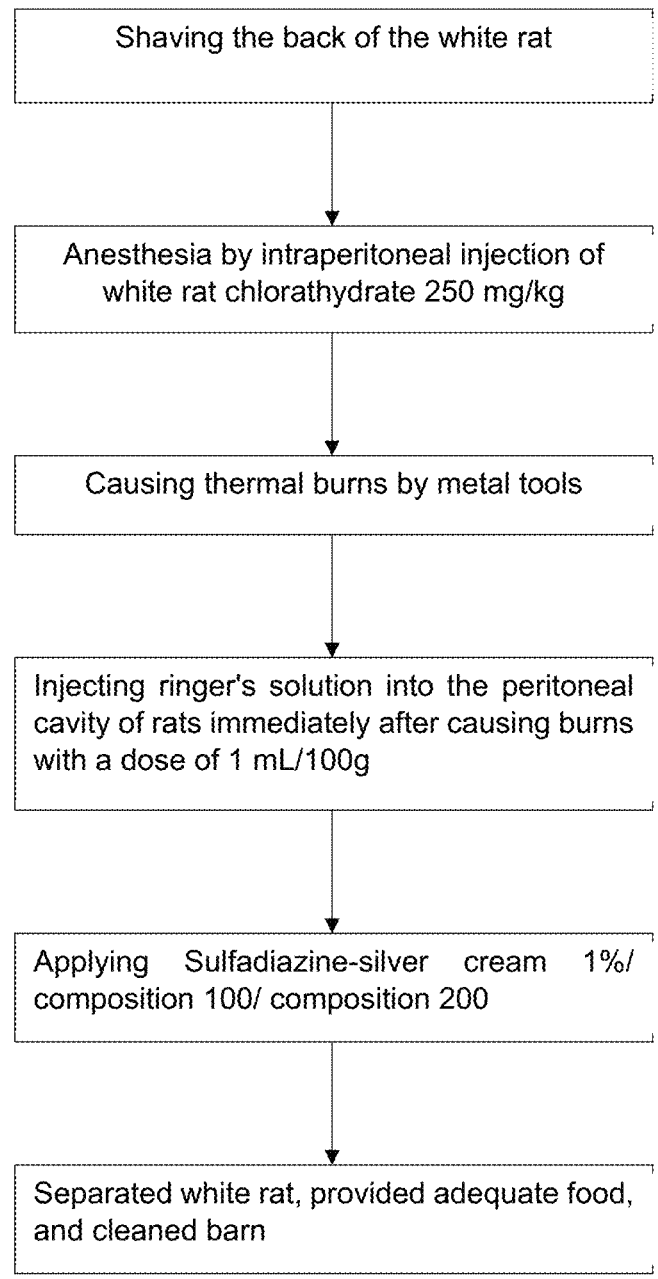
FIG. 2 is a process that causes thermal burns model on the skin of white rats.
Figure 3A:
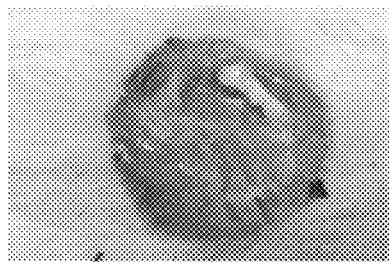
FIG. 3A-3C are macroscopic images of burn of the rat number 15 of Lot 2 after 7, 14, and 21 days of performing thermal burns model.
Figure 3B:
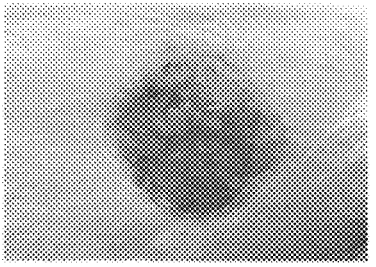
Figure 3C:
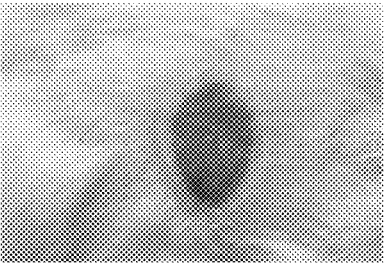
Figure 3D:
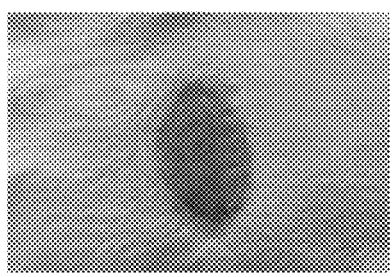
FIG. 3D-3F are macroscopic images of burn of the rat number 29 of Lot 3 after 7, 14, and 21 days of performing thermal burns model.
Figure 3E:
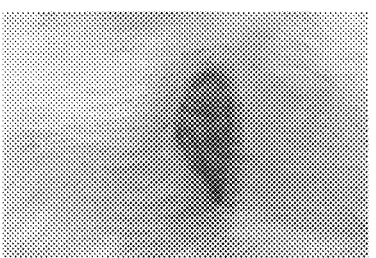
Figure 3F:
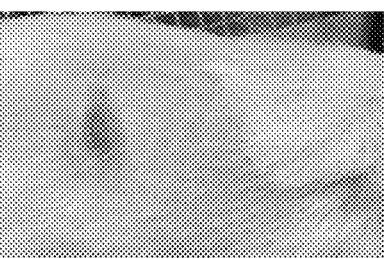
Figure 3G:
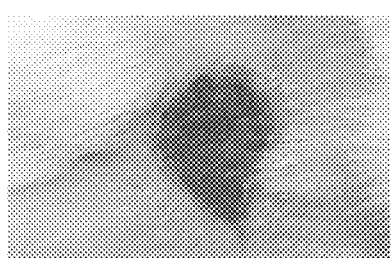
FIG. 3G-3I are macroscopic images of burn of the rat number 36 of Lot 4 after 7, 14, and 21 days of performing thermal burns model.
Figure 3H:
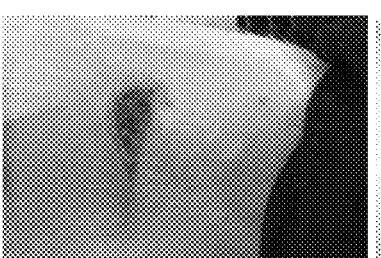
Figure 3I:
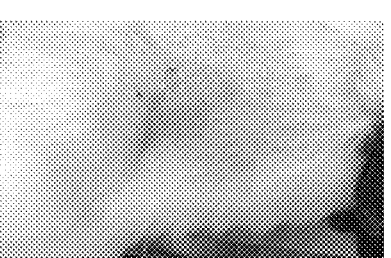
Figure 3J:
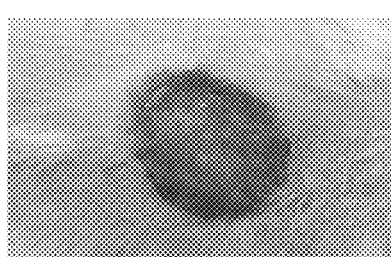
FIG. 3J-3L are macroscopic images of burn of the rat number 43 of Lot 5 after 7, 14, and 21 days of performing thermal burns model.
Figure 3K:
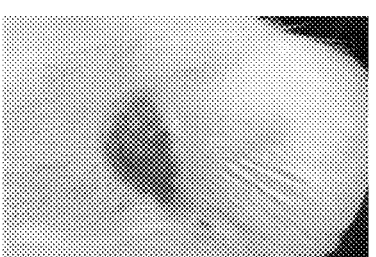
Figure 3L:
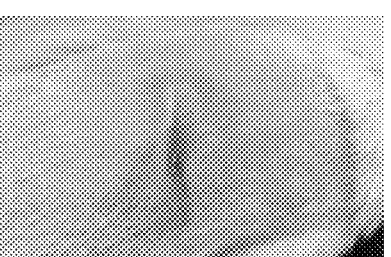

Rats in batches were subjected to dermal burn lesions according to the thermal burn model with metal tools as described by Durmus A S et al. as described by FIG. 2; wherein rats shaving position: the lower face is horizontal with 2 pelvic crests (rat thighs) from which cut up about 6 cm and widen on both sides about 3 cm to get an area of 6×6 cm shaved area. Instrument causing burns (weighing 200 g, diameter 2.5 cm) is immersed in boiling water of 100° C. until reaching a constant temperature, placed perpendicularly on the back of the mouse for 35 seconds and must not apply additional force from the outside.

Research indicators during burn treatment including: (A) macromorphological index, (B) quantification of hydroxyproline concentration in damaged tissue, and (C) micromorphic index; wherein:

(A) macromorphological index:
   Injury status at the burn: swelling, heat, redness, edema observed by eye and recorded by digital camera;
   Measure the burn area at 7, 14, and 21 days after causing the burn. Area measured by digital imaging at the same lens and focal length for all rats, measuring area using ImageJ Basics ver 1.38 software that has been recognized by the World Health Organization as software for measuring area measurement for biomedical research;

(B) quantification of hydroxyproline concentration in damaged tissue: the hydroxyproline content in the skin at the burn site was determined by the method of Stegemann H. and Stalder K, the process is summarized as follows:
   weigh approximately 20-30 mg of the skin sample and place it in a hydrolysis tube with a stopper;
   adding 2 ml of 6N HCl and incubated at 115° C.;
   after 24 hours, collecting the hydrolyzate and put it in a test tube; each test tube contains 0.2 ml of the sample hydrolyzate; 1.8 ml of distilled water; 1 ml of chloramine T solution;
   shaking and leave for 20 minutes at room temperature;
   next, adding 2 ml of 4M perchloric acid to each tube, shaking and leave for 5 min at room temperature, then adding 1 ml of a 10% solution of 4-dimethyl-amino benzaldehyde;
   shaking the tube and heating in a water bath at 60° C. for 15 min; cooling to room temperature and measuring the absorbance at 560 nm; and
   the content of hydroxylproline in the sample was determined based on the developed standard curve;

(C) micromorphic index:
   at the end of the study, when the burns had completely peeled off and were healing or healed, rats were anesthetized with chloralhydrate at a dose of 250 mg/kg, then histopathology was taken at the lesion site;
   evaluation of inflammation, fibroblast proliferation, vascular proliferation, and wound epithelialization;
   randomly examine the skin microstructure of 30% of the rat in each batch; and
   micromorphic tests were performed at the Department of Pathology—Hospital 103.

Results of the treatment effects of Sulfadiazine-silver cream 1%, composition 100, and composition 200 on the experimental burn model, listed in Table 1, and Table 2 below.

TABLE 1

Effect of composition 100, and composition 200 on burn area

| Rats lot | Burn area ($cm^2$) | | |
|---|---|---|---|
| | After 7 days ($\bar{x} \pm SD$) | After 14 days ($\bar{x} \pm SD$) | After 21 days Median (quartile) |
| Lot 2 | 4.198 ± 0.881 | 1.636 ± 0.504 | 0.104 (0.076; 0.445) |
| Lot 3 | 3.808 ± 0.871 | 1.066 ± 0.325 | 0.028 (0; 0.129) |
| p compare to Lot 2 | >0.05 | <0.01 | <0.05 |
| Lot 4 | 3.580 ± 0.462 | 0.590 ± 0.190 | 0.011 (0; 0.019) |
| p compare to Lot 2 | >0.05 | <0.001 | <0.01 |
| p compare to Lot 3 | >0.05 | <0.01 | <0.01 |
| Lot 5 | 3.848 ± 0.590 | 1.119 ± 0.336 | 0.074 (0.031; 0.107) |
| p compare to Lot 2 | >0.05 | <0.01 | <0.05 |
| p compare to Lot 3 | >0.05 | >0.05 | >0.05 |
| p compare to Lot 4 | >0.05 | <0.01 | <0.05 |

Note: Burn area at 7 days and 14 days after performed thermal burns model was analyzed using one-way variance (ONE WAY ANOVA), then use the Student-Newman-Keuls post-test to compare each pair. Burn area at 21 days after performed thermal burns model was analyzed using Kruskall-Wallis and Mann-Whitney U-test for pairwise comparison.

Based on Table 1, at 7 days after performed thermal burns model, burn area tends to narrow in Lot 3, Lot 4, and Lot 5 that compared to Lot 2; however, the difference was not statistically significant ($p>0.05$). At 14 days after performed thermal burns model, Lot 3, lot 4, and Lot 5 have the effect of reducing the burn area significantly compared to Lot 2, the difference was statistically significant with $p<0.01$; wherein the burn area in Lot 4 application was narrower than in Lot 5 batch, the difference was statistically significant with $p<0.01$. At 21 days after performed thermal burns model, Lot 3, lot 4, and Lot 5 have the effect of reducing the burn area significantly compared to Lot 2, the difference was statistically significant with $p<0.05$; wherein the burn area in Lot 4 application was narrower than in Lot 5 batch, the difference was statistically significant with $p<0.05$.

TABLE 2

Effect of composition 100, and composition 200 on hydroxyproline concentrations in rat skin.

| Rats lot | Hydroxyproline concentrations in rat skin (mg/g skin) ($\bar{x} \pm SD$) |
|---|---|
| Lot 1 | 35.53 ± 6.20 |
| Lot 2 | 15.99 ± 5.00 |
| p compare to Lot 1 | <0.001 |
| Lot 3 | 25.91 ± 3.40 |
| p compare to Lot 1 | <0.05 |
| p compare to Lot 2 | <0.01 |
| Lot 4 | 34.03 ± 7.27 |
| p compare to Lot 1 | >0.05 |
| p compare to Lot 2 | <0.001 |
| p compare to Lot 3 | <0.05 |
| Lot 5 | 29.77 ± 7.22 |
| p compare to Lot 1 | >0.05 |
| p compare to Lot 2 | <0.001 |
| p compare to Lot 3 | >0.05 |
| p compare to Lot 4 | >0.05 |

Based on Table 2, after 21 days of inducing burn model, the concentration of hydroxyproline in the rat skin of Lot 2 was significantly reduced compared with that of Lot 1, the difference was statistically significant with p<0.001. The concentration of hydroxyproline in the rat skin of Lot 3 increased compared with that of Lot 1, the difference was statistically significant with p<0.01. The concentration of hydroxyproline in the rat skin of Lot 4 and Lot 5 increased compared with that of Lot 1, the difference was statistically significant with p<0.001. There was no statistically significant difference in rat skin hydroxyproline concentrations between Lot 4 and Lot 5.

The results of the macroscopic images of burns at the study time points (7, 14, and 21 days) are referenced by FIG. 3A-3L. Immediately after applying performed thermal burns model: the burn is ivory-white, without blistering, clearly demarcated with healthy skin. About 1-2 hours later, the margin around the burn is clearly visible. After 3 days, 100% of the burns ulcerated. The burn is in a necrotic state, with many ulcers on the surface. The sores gradually widen, containing a lot of secretions. The area around the burn is edematous, but still has a boundary with the healthy skin. At 7 days, the ulcers in the model mice still secreted a lot of fluid. The skin around the burn remains congested. The burns of rats applied Lot 3, Lot 4, and Lot 5 were dry and non-exudative, and the burn injury area was narrower than that of Lot 2. At 14 days, the burns all formed scabs, the burns began to scab to reveal the healing area below, the burns were dry. The skin around the lesion is no longer congested. After 21 days, all the burns were scabbed, the burns were dry, and the damaged skin area was significantly reduced in the reagent lot compared to Lot 2.

The results of the micromorphic images of burns at the study time points (7, 14, and 21 days) including:

Lot 1 has the following characteristics: Normal skin structure, skin covered with stratified squamous epithelium with keratinized, clearly basal membrane structure, normal skin dependent glands;

Lot 2 has the following characteristics: the skin structure has many areas of loss of epithelium covering the superficial dermis; the leukocyte silk-coated surface has quite a few neutrophil inflammatory cells;

Lot 3 and Lot 4 have the following characteristics: the burned skin formed epithelialized fibrous scars; and Lot 5 has the following characteristics: the burned skin formed epithelialized fibrous scars; however, there are still skin biopsies with ulcers covering the superficial dermis with the ulcer surface covered with leukocyte fibrils containing many neutrophil inflammatory cells.

Figure 4A:
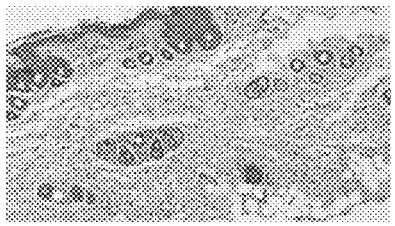
FIG. 4A is micromorphic images of burns of Lot 1 (the rat number 01)
Figure 4B:
FIG. 4B is micromorphic images of burns of Lot 1 (the rat number 02)
Figure 4C:
FIG. 4C is micromorphic images of burns of Lot 1 (the rat number 04)
Figure 4D:
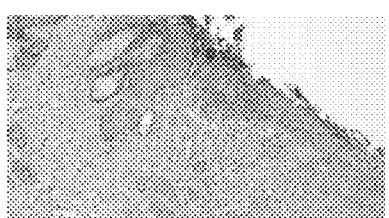
FIG. 4D is micromorphic images of burns of Lot 1 (the rat number 12)
Figure 4E:
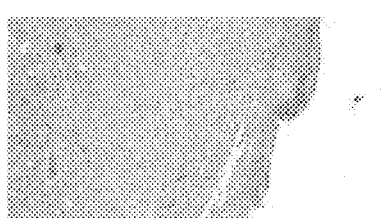
FIG. 4E is micromorphic images of burns of Lot 1 (the rat number 15)
Figure 4F:
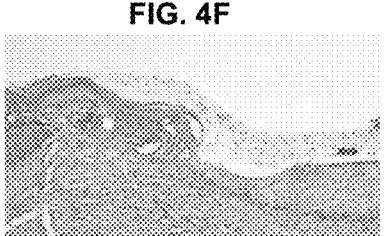
FIG. 4F is micromorphic images of burns of Lot 1 (the rat number 16)
Figure 4G:
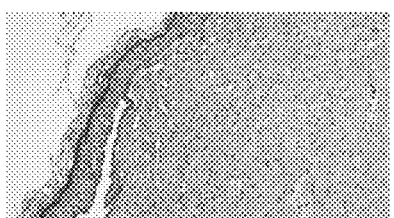
FIG. 4G is micromorphic images of burns of Lot 3 (the rat number 21)
Figure 4H:
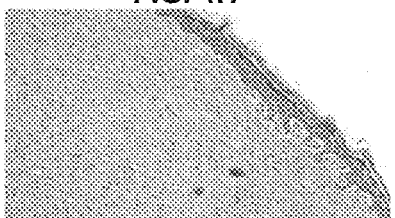
FIG. 4H is micromorphic images of burns of Lot 3 (the rat number 27)
Figure 4I:
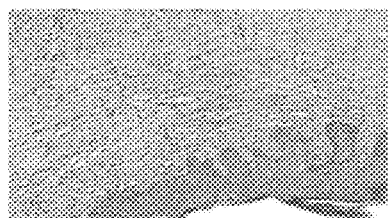
FIG. 4I is micromorphic images of burns of Lot 3 (the rat number 29)
Figure 4J:
FIG. 4J is micromorphic images of burns of Lot 4 (the rat number 32)
Figure 4K:
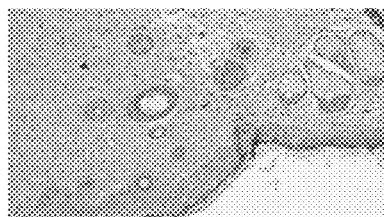
FIG. 4K is micromorphic images of burns of Lot 4 (the rat number 36)
Figure 4L:
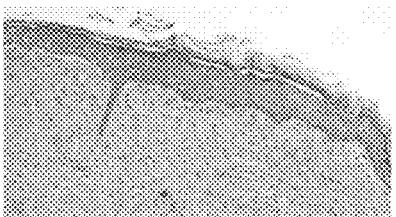
FIG. 4L is micromorphic images of burns of Lot 4 (the rat number 37)
Figure 4M:
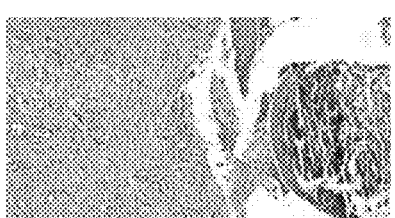
FIG. 4M is micromorphic images of burns of Lot 5 (the rat number 41)
Figure 4N:
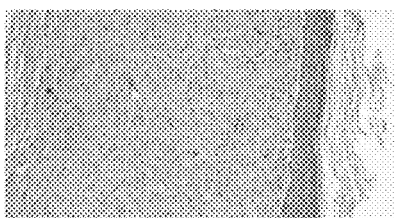
FIG. 4N is micromorphic images of burns of Lot 5 (the rat number 43)
Figure 4O:
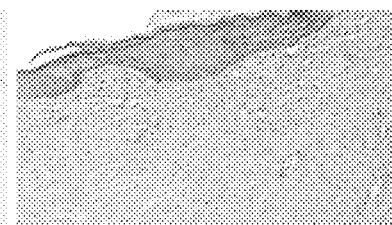
FIG. 4O is micromorphic images of burns of Lot 5 (the rat number 45)

Referring to FIG. 4A-4C, all of the micromorphic images of burns has the following characteristics: normal skin structure; the skin covered with stratified squamous epithelium is keratinized, well-layered structure, well-structured basement membrane, well-structured skin accessory components; and the stromal tissue has collagenous fibers, elastic fibers, and blood vessels.

Referring to FIG. 4D-4F and FIG. 4M, all of the micromorphic images of burns has the following characteristics: the surface of the skin loses the epithelium covering the superficial dermis; the leukocyte silk-coated surface is abundant with neutrophil inflammatory cells, and granulomatous formation begins at the margin of the ulcer with many proliferating blood vessels.

Referring to FIG. 4G-4L and FIG. 4N-4O, all of the micromorphic images of burns has the following characteristics: biopsy of stratified squamous epithelium is keratinized, with few dermal papillae and short epidermal crest, and the basement membrane is clear and fairly straight; the superficial dermis is a proliferative callus with many fibroblasts, collagenous fibers, and mononuclear inflammatory cells.

Results experiment of evaluation of the systemic effects of composition 100 and composition 200 on burned white rats, including: (A1) General condition and body weight change of rats; (A2) Evaluation of hematopoietic function, (A3) Assess the extent of liver cell damage; (A4) Assessment of liver function, (A5) Assess kidney function, and (A6) Histopathological changes (macroscopic, microscopic).

(A1) General condition and body weight change of rats: During the experiment, rats in Lot 1, Lot 4, and Lot 5 were active, agile, bright eyes, and dry stools. No special expression was observed in all 3 Lots of rats during the study period. Results effect of composition 100 and composition 200 on rat body weight listed in Table 3 below. After 10 days and 21 days of burn modeling, there was no statistically significant difference in rat weight between Lot 1 with Lot 4 and Lot 5 (p>0.05).

TABLE 3

Effect of the composition 100 and the composition 200 on rat body weight

| Rat lot | Weight (gam) | | |
|---|---|---|---|
| | Before research | After 10 days | After 21 days |
| Lot 1 | 181.50 ± 15.99 | 202.50 ± 19.61 | 212.50 ± 25.08 |
| Lot 4 | 185.00 ± 13.54 | 203.00 ± 14.94 | 208.00 ± 19.32 |
| p compare to Lot 1 | >0.05 | >0.05 | >0.05 |
| Lot 5 | 179.00 ± 13.70 | 196.00 ± 14.30 | 201.00 ± 19.55 |
| p compare to Lot 1 | >0.05 | >0.05 | >0.05 |

(A2)-(A5) based on standards including: red blood cell count, hemoglobin content, hematocrit content, mean erythrocyte volume, white blood cell count, white blood cell formula, platelet count, AST activity, ALT activity, total bilirubin concentration, albumin concentration, total cholesterol concentration, and creatinine concentration. All said standards of Lot 4 and Lot 5 had no statistically significant difference compared with Lot 1 and compared between at times before and after applying the composition 100/composition 200 (p>0.05) (referenced by Table 4-15 below).

TABLE 4

Effect of the composition 100 and the composition 200 on red blood cell count.

| Rat lot | red blood cell counts (T/I) | | | $P_{before-after}$ |
|---|---|---|---|---|
| | Before research | After 10 days | After 21 days | |
| Lot 1 | 8.74 ± 0.50 | 8.63 ± 0.98 | 9.29 ± 0.67 | >0.05 |
| Lot 4 | 9.03 ± 0.50 | 8.37 ± 1.09 | 9.56 ± 0.71 | >0.05 |
| p compare to Lot 1 | >0.05 | >0.05 | >0.05 | |
| Lot 5 | 8.29 ± 0.98 | 8.76 ± 1.17 | 9.14 ± 1.24 | >0.05 |
| p compare to Lot 1 | >0.05 | >0.05 | >0.05 | |

TABLE 5

Effect of the composition 100 and the composition 200 on hemoglobin content count.

| | The hemoglobin content (g/dl) | | | |
|---|---|---|---|---|
| Rat lot | Before research | After 10 days | After 21 days | $P_{before-after}$ |
| Lot 1 | 11.14 ± 0.79 | 10.87 ± 0.55 | 11.75 ± 0.66 | >0.05 |
| Lot 4 | 11.74 ± 0.88 | 10.94 ± 1.32 | 11.85 ± 1.01 | >0.05 |
| p compare to Lot 1 | >0.05 | >0.05 | >0.05 | |
| Lot 5 | 11.02 ± 0.88 | 10.84 ± 1.05 | 11.56 ± 0.86 | >0.05 |
| p compare to Lot 1 | >0.05 | >0.05 | >0.05 | |

TABLE 6

Effect of the composition 100 and the composition 200 on hematocrit count.

| | Hematocrit (%) | | | |
|---|---|---|---|---|
| Rat lot | Before research | After 10 days | After 21 days | $P_{before-after}$ |
| Lot 1 | 46.53 ± 3.11 | 45.21 ± 3.44 | 48.74 ± 2.99 | >0.05 |
| Lot 4 | 48.95 ± 3.19 | 47.51 ± 3.72 | 50.63 ± 3.80 | >0.05 |
| p compare to Lot 1 | >0.05 | >0.05 | >0.05 | |
| Lot 5 | 48.32 ± 4.96 | 47.80 ± 3.38 | 50.21 ± 2.26 | >0.05 |
| p compare to Lot 1 | >0.05 | >0.05 | >0.05 | |

TABLE 7

Effect of the composition 100 and the composition 200 on mean erythrocyte volume.

| | mean erythrocyte volume (fl) | | | |
|---|---|---|---|---|
| Rat lot | Before research | After 10 days | After 21 days | $P_{before-after}$ |
| Lot 1 | 53.00 ± 1.83 | 52.30 ± 1.64 | 52.40 ± 1.90 | >0.05 |
| Lot 4 | 52.50 ± 1.84 | 51.70 ± 2.21 | 52.80 ± 1.75 | >0.05 |
| p compare to Lot 1 | >0.05 | >0.05 | >0.05 | |
| Lot 5 | 51.90 ± 1.37 | 50.60 ± 2.67 | 51.60 ± 1.84 | >0.05 |
| p compare to Lot 1 | >0.05 | >0.05 | >0.05 | |

TABLE 8

Effect of the composition 100 and the composition 200 on white blood cell count.

| | white blood cell count (G/l) | | | |
|---|---|---|---|---|
| Rat lot | Before research | After 10 days | After 21 days | $P_{before-after}$ |
| Lot 1 | 6.77 ± 1.34 | 7.26 ± 1.17 | 7.68 ± 0.87 | >0.05 |
| Lot 4 | 6.52 ± 1.96 | 6.85 ± 1.83 | 7.43 ± 1.64 | >0.05 |
| p compare to Lot 1 | >0.05 | >0.05 | >0.05 | |
| Lot 5 | 6.67 ± 1.11 | 7.54 ± 1.53 | 7.71 ± 1.84 | >0.05 |
| p compare to Lot 1 | >0.05 | >0.05 | >0.05 | |

TABLE 9

Effect of the composition 100 and the composition 200 on the white blood cell formula.

| | The white blood cell formula | | | | | |
|---|---|---|---|---|---|---|
| | Lot 1 | | Lot 4 | | Lot 5 | |
| Time | Lymphocytes (%) | Neutrophil (%) | Lymphocytes (%) | Neutrophil (%) | Lymphocytes (%) | Neutrophil (%) |
| Before research | 76.57 ± 3.82 | 14.93 ± 3.18 | 74.45 ± 3.18 | 13.48 ± 2.99 | 72.84 ± 4.78 | 15.36 ± 2.85 |
| After 10 days | 77.16 ± 4.18 | 13.74 ± 2.95 | 74.27 ± 4.72 | 12.96 ± 4.26 | 73.17 ± 5.85 | 13.49 ± 3.58 |
| $P_{before-after}$ | >0.05 | >0.05 | >0.05 | >0.05 | >0.05 | >0.05 |
| After 21 days | 74.72 ± 6.17 | 12.87 ± 4.02 | 70.41 ± 8.45 | 13.91 ± 4.21 | 69.41 ± 7.01 | 14.77 ± 4.68 |
| $P_{before-after}$ | >0.05 | >0.05 | >0.05 | >0.05 | >0.05 | >0.05 |

TABLE 10

Effect of the composition 100 and the composition 200 on the platelet count.

| | Platelet count (G/l) | | | |
|---|---|---|---|---|
| Rat lot | Before research | After 10 days | After 21 days | $P_{before-after}$ |
| Lot 1 | 527.70 ± 92.24 | 546.70 ± 89.19 | 532.00 ± 88.15 | >0.05 |
| Lot 4 | 590.60 ± 97.91 | 510.90 ± 88.16 | 602.50 ± 93.89 | >0.05 |
| p compare to Lot 1 | >0.05 | >0.05 | >0.05 | |
| Lot 5 | 509.40 ± 96.59 | 529.10 ± 101.56 | 515.10 ± 85.62 | >0.05 |
| p compare | >0.05 | >0.05 | >0.05 | |

TABLE 10-continued

Effect of the composition 100 and the composition 200 on the platelet count.

| | Platelet count (G/l) | | | |
|---|---|---|---|---|
| Rat lot | Before research | After 10 days | After 21 days | $P_{before-after}$ |
| to Lot 1 | | | | |

TABLE 11

Effect of the composition 100 and the composition 200 on the AST activity.

| | AST activity (UI/l) | | | |
|---|---|---|---|---|
| Rat lot | Before research | After 10 days | After 21 days | $P_{before-after}$ |
| Lot 1 | 80.40 ± 7.49 | 77.00 ± 8.81 | 74.70 ± 8.93 | >0.05 |
| Lot 4 | 81.90 ± 6.97 | 79.10 ± 7.49 | 76.20 ± 7.11 | >0.05 |
| p compare to Lot 1 | >0.05 | >0.05 | >0.05 | |
| Lot 5 | 79.50 ± 7.72 | 78.90 ± 9.42 | 75.70 ± 11.91 | >0.05 |
| p compare to Lot 1 | >0.05 | >0.05 | >0.05 | |

TABLE 12

Effect of the composition 100 and the composition 200 on the ALT activity.

| | ALT activity (UI/l) | | | |
|---|---|---|---|---|
| Rat lot | Before research | After 10 days | After 21 days | $P_{before-after}$ |
| Lot 1 | 38.40 ± 6.74 | 35.30 ± 7.78 | 34.50 ± 5.99 | >0.05 |
| Lot 4 | 40.50 ± 3.37 | 37.70 ± 5.56 | 37.90 ± 3.90 | >0.05 |
| p compare to Lot 1 | >0.05 | >0.05 | >0.05 | |
| Lot 5 | 41.70 ± 4.16 | 41.00 ± 4.90 | 39.10 ± 4.89 | >0.05 |
| p compare to Lot 1 | >0.05 | >0.05 | >0.05 | |

TABLE 13

Effect of the composition 100 and the composition 200 on the total bilirubin concentration.

| | Total bilirubin concentration (mmol/l) | | | |
|---|---|---|---|---|
| Rat lot | Before research | After 10 days | After 21 days | $P_{before-after}$ |
| Lot 1 | 9.14 ± 0.64 | 9.38 ± 0.75 | 9.27 ± 0.75 | >0.05 |
| Lot 4 | 9.63 ± 0.84 | 9.68 ± 0.92 | 9.54 ± 1.08 | >0.05 |
| p compare to Lot 1 | >0.05 | >0.05 | >0.05 | |
| Lot 5 | 9.43 ± 0.78 | 9.17 ± 0.68 | 9.33 ± 0.42 | >0.05 |
| p compare to Lot 1 | >0.05 | >0.05 | >0.05 | |

TABLE 14

Effect of the composition 100 and the composition 200 on the albumin concentration.

| | Albumin concentration (g/dl) | | | |
|---|---|---|---|---|
| Rat lot | Before research | After 10 days | After 21 days | $P_{before-after}$ |
| Lot 1 | 3.17 ± 0.46 | 3.22 ± 0.24 | 3.07 ± 0.27 | >0.05 |
| Lot 4 | 3.36 ± 0.28 | 3.15 ± 0.28 | 3.14 ± 0.29 | >0.05 |

TABLE 14-continued

Effect of the composition 100 and the composition 200 on the albumin concentration.

| | Albumin concentration (g/dl) | | | |
|---|---|---|---|---|
| Rat lot | Before research | After 10 days | After 21 days | $P_{before-after}$ |
| p compare to Lot 1 | >0.05 | >0.05 | >0.05 | |
| Lot 5 | 3.07 ± 0.26 | 3.19 ± 0.23 | 2.92 ± 0.29 | >0.05 |
| p compare to Lot 1 | >0.05 | >0.05 | >0.05 | |

TABLE 15

Effect of the composition 100 and the composition 200 on the total cholesterol concentration.

| | Total cholesterol concentration (mmol/l) | | | |
|---|---|---|---|---|
| Rat lot | Before research | After 10 days | After 21 days | $P_{before-after}$ |
| Lot 1 | 1.43 ± 0.25 | 1.38 ± 0.10 | 1.49 ± 0.21 | >0.05 |
| Lot 4 | 1.57 ± 0.22 | 1.45 ± 0.15 | 1.60 ± 0.15 | >0.05 |
| p compare to Lot 1 | >0.05 | >0.05 | >0.05 | |
| Lot 5 | 1.35 ± 0.12 | 1.40 ± 0.18 | 1.46 ± 0.19 | >0.05 |
| p compare to Lot 1 | >0.05 | >0.05 | >0.05 | |

TABLE 16

Effect of the composition 100 and the composition 200 on the creatinine concentration.

| | creatinine concentration (mg/dl) | | | |
|---|---|---|---|---|
| Rat lot | Before research | After 10 days | After 21 days | $P_{before-after}$ |
| Lot 1 | 0.80 ± 0.11 | 0.90 ± 0.15 | 0.87 ± 0.13 | >0.05 |
| Lot 4 | 0.83 ± 0.14 | 0.85 ± 0.16 | 0.90 ± 0.11 | >0.05 |
| p compare to Lot 1 | >0.05 | >0.05 | >0.05 | |
| Lot 5 | 0.83 ± 0.11 | 0.86 ± 0.16 | 0.89 ± 0.16 | >0.05 |
| p compare to Lot 1 | >0.05 | >0.05 | >0.05 | |

(A6) Histopathological changes based on standards including: macroscopic, and micromorphic. For macroscopic: in all experimental rats (both Lot 1, Lot 4, and Lot 5) do not gross pathological changes were observed in the heart, lung, liver, spleen, pancreas, kidney and gastrointestinal organs of rats.

Figure 5A:
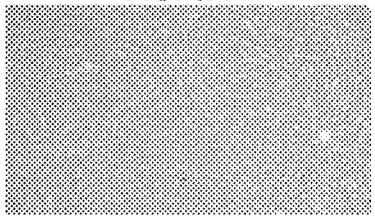
FIG. 5A is a microscopic image of the liver of the rat Lot 1 (Rat number 1); normal hepatocytes (Hematoxylin—Eosin staining)
Figure 5B:
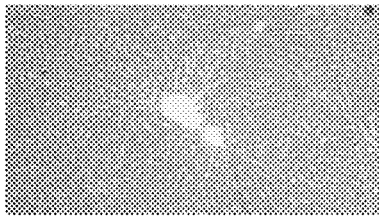
FIG. 5B is a microscopic image of the liver of the rat Lot 1 (Rat number 2); normal hepatocytes.
Figure 5C:
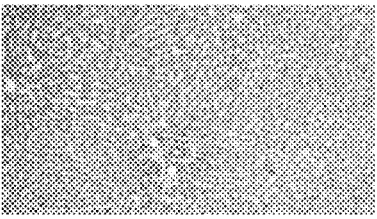
FIG. 5C is a microscopic image of the liver of the rat Lot 1 (Rat number 4); normal hepatocytes.
Figure 5D:
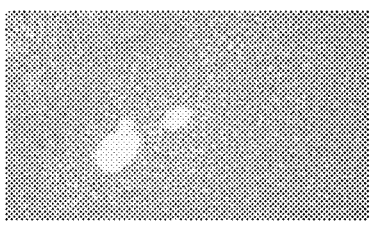
FIG. 5D is a microscopic image of the liver of the rat Lot 4 (Rat number 32); normal hepatocytes.
Figure 5E:
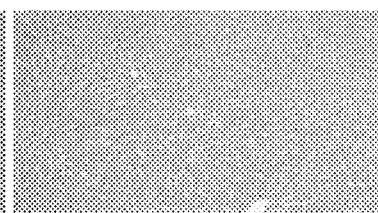
FIG. 5E is a microscopic image of the liver of the rat Lot 4 (Rat number 36); normal hepatocytes.
Figure 5F:
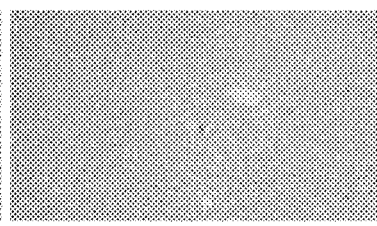
FIG. 5F is a microscopic image of the liver of the rat Lot 4 (Rat number 37); normal hepatocytes.
Figure 5G:
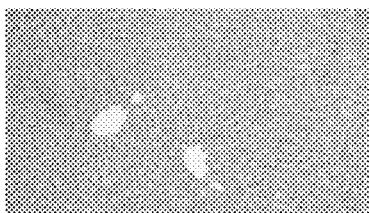
FIG. 5G is a microscopic image of the liver of the rat Lot 5 (Rat number 41); normal hepatocytes.
Figure 5H:
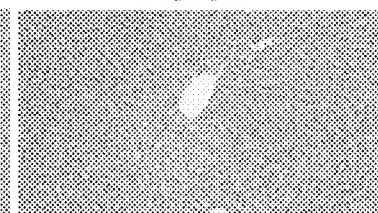
FIG. 5H is a microscopic image of the liver of the rat Lot 5 (Rat number 43); normal hepatocytes.
Figure 5I:
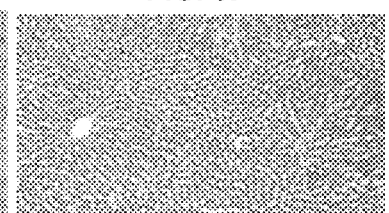
FIG. 5I is a microscopic image of the liver of the rat Lot 5 (Rat number 45); normal hepatocytes.
Figure 5J:
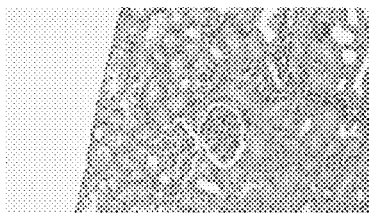
FIG. 5J is a microscopic image of the kidney of the rat Lot 1 (Rat number 1); normal hepatocytes.
Figure 5K:
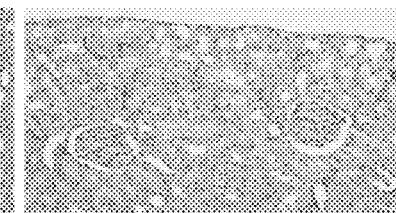
FIG. 5K is a microscopic image of the kidney of the rat Lot 1 (Rat number 2); normal hepatocytes.
Figure 5L:
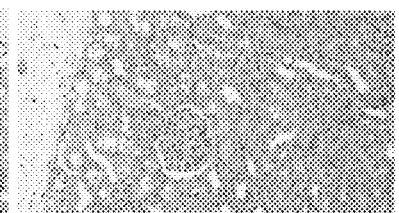
FIG. 5L is a microscopic image of the kidney of the rat Lot 1 (Rat number 4); normal hepatocytes.
Figure 5M:
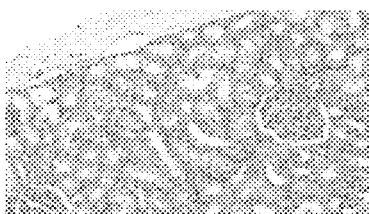
FIG. 5M is a microscopic image of the kidney of the rat Lot 4 (Rat number 32); normal hepatocytes.
Figure 5N:
FIG. 5N is a microscopic image of the kidney of the rat Lot 4 (Rat number 36); normal hepatocytes.
Figure 5O:
FIG. 5O is a microscopic image of the kidney of the rat Lot 4 (Rat number 37); normal hepatocytes.
Figure 5P:
FIG. 5P is a microscopic image of the kidney of the rat Lot 5 (Rat number 41); normal hepatocytes.
Figure 5Q:
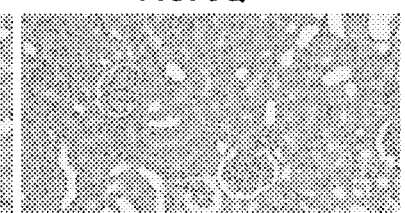
FIG. 5Q is a microscopic image of the kidney of the rat Lot 5 (Rat number 43); normal hepatocytes.
Figure 5R:
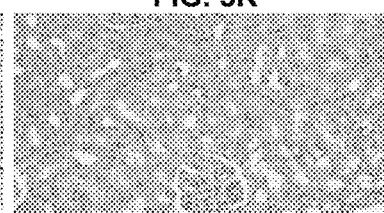
FIG. 5R is a microscopic image of the kidney of the rat Lot 5 (Rat number 45); normal hepatocytes.

Result microscopic images of the rat liver of Lot 1, Lot 4, and Lot 5 referenced from FIG. 5A to FIG. 5R, showed that the hepatocytes and renal cells were functioning normally.

Summary Results of Burn Treatment:

Burn treatment effects of the composition 100 and composition 200 on experimental thermal burn model: The composition 100 and composition 200 applied at a dose of 0.3 ml/burn/time, 2 times/day had the effect of treating experimental burns shown by reducing the burn area, increasing the concentration of hydroxyprolin in the skin compared with the Lot 2 after 21 days of causing burns; The composition 100 has better burn treatment effect than The composition 200 on experimental burn model;

Systemic effects of the composition 100 and composition 200 applied on skin on experimental burn model:

Both the compositions did not affect the general condition, the level of weight gain of rat compared with the Lot 1;

Does not change the results of tests to evaluate hematopoietic function (red blood cell count, hemoglobin content, hematocrit, mean red blood cell volume, white blood cell count, white blood cell formula, platelet count) compared with the Lot 1;

Did not change the results of liver function tests (concentrations of total bilirubin, albumin and total cholesterol in the blood of rats) compared with the Lot 1. No hepatocellular damage (AST, ALT activity in rat blood) compared with Lot 1;

Does not change the test results of creatinine in the blood of rats after 21 days of continuous reagent use compared to the Lot 1; and There was no morphological damage when observing the gross organs of rat compared with the Lot 1. Microstructure of liver and kidney of rats: There was no significant difference compared with Lot 1 after 21 days of continuous said composition use in a skin burn model.

Evaluation of the scar healing effect of the composition 100 and composition 200 in experiments. The model was based on previous studies of doxorubicin-induced skin ulcers in white mice of Swiss strain, both breeds, healthy, weight 30-35 g. White mice of both breeds of both breeds were randomly divided into 5 lots, each batch of 10 animals as follows:

Lot 1: Intradermal injection of physiological saline, no applying DMSO/composition 100/composition 200;

Lot 2: Intradermal injection of doxorubicin 1 mg/0.5 ml, to heal the ulcer naturally;

Lot 3: Intradermal injection of doxorubicin 1 mg/0.5 ml, for ulcer progression for 7 days. Then, drop 0.1 ml of DMSO on the ulcerated area, 2 times a day, use within 21 days;

Lot 4: Intradermal injection of doxorubicin 1 mg/0.5 ml, for ulcer progression for 7 days. Then, apply the composition 100 with dose of 0.1 ml/ulcer/time, 2 times/day, used for 21 days; and Lot 5: Intradermal injection of doxorubicin 1 mg/0.5 ml, for ulcer progression for 7 days. Then, apply the composition 200 with dose of 0.1 ml/ulcer/time, with a frequency of twice daily, and used for 21 days.

Research indicators during scar healing including: (A) macromorphological index, (B) quantification of hydroxyproline concentration in damaged tissue, and (C) micromorphic index; all was samed as the burn treatment research experimental.

Results of the scar healing effects of DMSO, composition 100, and composition 200 on the model of skin damage, listed in Table 17-18 below.

TABLE 17

Effect of composition 100, and composition 200 to the area of skin ulcers on the skin of white mice.

| | Area of skin ulcers (mm$^2$) | | | |
| --- | --- | --- | --- | --- |
| Rats lot | Before applied ($\bar{x} \pm SD$) | After 7 days ($\bar{x} \pm SD$) | After 14 days Median (quartile) | After 21 days Median (quartile) |
| Lot 2 | 73.30 ± 14.56 | 64.18 ± 13.05 | 17.58 [8.91; 31.69] | 16.42 [0; 21.02] |
| Lot 3 | 75.71 ± 14.02 | 50.13 ± 12.55 | 7.13 [0; 9.54] | 0 [0; 8,37] |
| p compare to Lot 2 | >0.05 | <0.05 | <0.05 | <0.05 |
| Lot 4 | 68.23 ± 16.94 | 50.54 ± 11.01 | 6.71 | 0 |

TABLE 17-continued

Effect of composition 100, and composition 200 to the area of skin ulcers on the skin of white mice.

| | Area of skin ulcers (mm$^2$) | | | |
| --- | --- | --- | --- | --- |
| Rats lot | Before applied ($\bar{x} \pm SD$) | After 7 days ($\bar{x} \pm SD$) | After 14 days Median (quartile) | After 21 days Median (quartile) |
| | | | [0; 10.70] | [0; 0.74] |
| p compare to Lot 2 | >0.05 | <0.05 | <0.01 | <0.05 |
| p compare to Lot 3 | >0.05 | >0.05 | >0.05 | >0.05 |
| Lot 5 | 70.83 ± 14.55 | 49.92 ± 9.57 | 10.19 [0; 15.59] | 0 [0; 11.40] |
| p compare to Lot 2 | >0.05 | <0.05 | <0.01 | <0.05 |
| p compare to Lot 3 | >0.05 | >0.05 | >0.05 | >0.05 |
| p compare to Lot 4 | >0.05 | >0.05 | >0.05 | >0.05 |

Note: area of skin ulcers at 7 days and 14 days after performed thermal burns model was analyzed using one-way variance (ONE WAY ANOVA), then use the Student-Newman-Keuls post-test to compare each pair. Burn area at 21 days after performed thermal burns model was analyzed using Kruskall-Wallis and Mann-Whitney U-test for pairwise comparison.

Based on Table 17, at the time before applied, the area of skin ulcers did not differ between the study Lots (p>0.05). After 7 days, the area of ulcers in the Lot 3, Lot 4 and Lot 5 were significantly reduced compared with the Lot 2 (p<0.05); wherein there was no statistically significant difference related to the area of skin ulcers in the Lot 4 and Lot 5 (p>0.05). At the time of 14 days and 21 days of applied DMSO, the composition 100, and composition 200; all had the effect of reducing the area of ulcers significantly compared to the Lot 2 at the same time, the difference was statistically significant (p<0.05); wherein there was no statistically significant difference related to the area of skin ulcersin the Lot 4 and Lot 5 (p>0.05) at the two study time points.

TABLE 18

Effect of composition 100, and composition 200 on hydroxyproline concentrations in rat skin.

| Rats lot | Hydroxyproline concentrations in rat skin (mg/g skin) ($\bar{x} \pm SD$) |
| --- | --- |
| Lot 1 | 17.04 ± 5.62 |
| Lot 2 | 10.24 ± 1.89 |
| p compare to Lot 1 | <0.01 |
| Lot 3 | 15.04 ± 2.35 |
| p compare to Lot 1 | >0.05 |
| p compare to Lot 2 | <0.05 |
| Lot 4 | 14.34 ± 2.18 |
| p compare to Lot 1 | >0.05 |
| p compare to Lot 2 | <0.05 |
| p compare to Lot 3 | >0.05 |
| Lot 5 | 13.89 ± 2.88 |
| p compare to Lot 1 | >0.05 |
| p compare to Lot 2 | <0.05 |
| p compare to Lot 3 | >0.05 |
| p compare to Lot 4 | >0.05 |

Based on Table 18, at the end of the study, the concentration of hydroxyprolin in the mice skin of the Lot 2 was significantly reduced compared with the Lot 1, the difference was statistically significant (p<0.01). The concentration of hydroxyprolin in the mice skin of the Lot 3 increased statistically significantly compared with the Lot 2 (p<0.05). The concentration of hydroxyprolin in the mice skin of the Lot 4 and Lot 5 increased significantly compared to the Lot 2 (p<0.05). There was no difference in hydroxyprolin concentrations in mice skin between the Lot 4 and Lot 5.

Figure 6A:
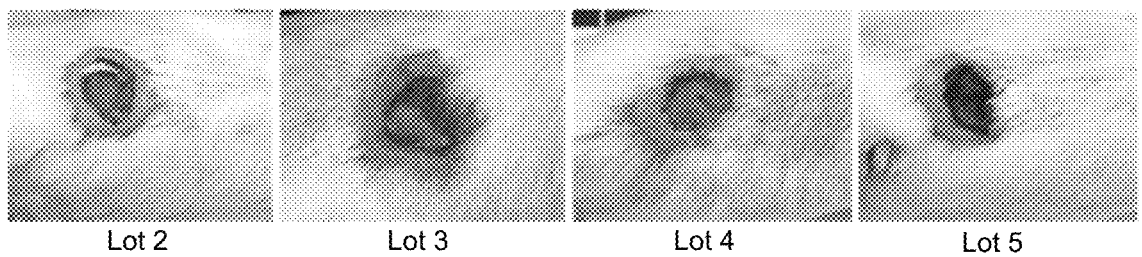
FIG. 6A is a macroscopic images of ulcers before applied of Lot 2, Lot 3, Lot 4, and Lot 5.
Figure 6B:
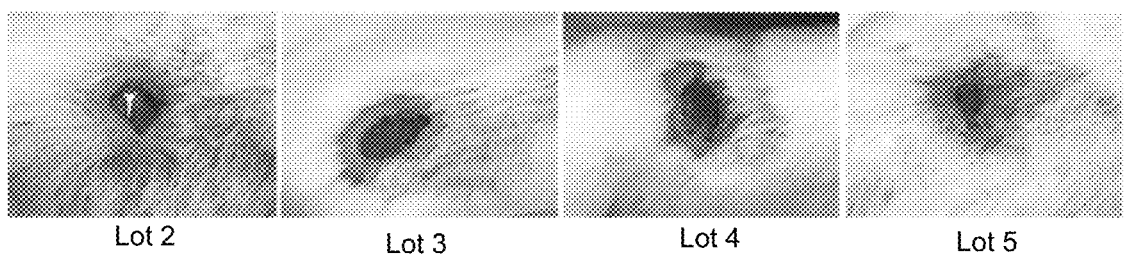
FIG. 6B is a macroscopic images of ulcers after 7 days applied of Lot 2, Lot 3, Lot 4, and Lot 5.
Figure 6C:
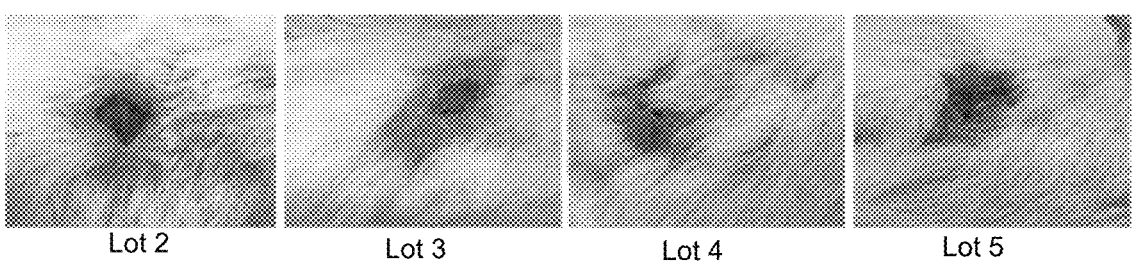
FIG. 6C is a macroscopic images of ulcers after 14 days applied of Lot 2, Lot 3, Lot 4, and Lot 5.
Figure 6D:
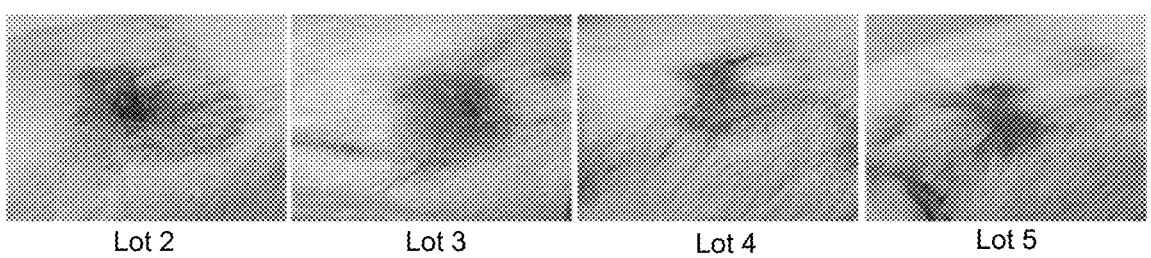
FIG. 6D is a macroscopic images of ulcers after 21 days applied of Lot 2, Lot 3, Lot 4, and Lot 5.

The results of the macroscopic images of ulcers at the study time points (before applied, 7, 14, and 21 days) are referenced by FIG. 6A. At the end of the study, the skin of mice had not yet completely healed the ulcer, with a large area of ulcers. The ulcerated skin area of mice of Lot 3, Lot 4, and Lot 5 was significantly reduced and almost completely healed skin ulcers. Details of the mice skin macroscopic images of ulcers of Lot 2-Lot 5 are referenced by FIG. 6A-6D.

The results of the micromorphic images of the skin at the ulcer including:

Lot 1 has the following characteristics: normal skin structure. Skin covered with stratified squamous epithelium, clear basement membrane structure, normal skin-dependent glands;

Lot 2 has the following characteristics: the skin has bands with deep ulcers in many areas, losing the entire epidermis, only a fibrous band and clusters of inflammatory cells remain, no blood vessels, there are many times keratinized area, some cells atrophy;

Lot 3 and Lot 4 have the following characteristics: the skin has regenerated to form the epidermis, no formation of skin-dependent glands, less blood vessels; and Lot 5 has the following characteristics: the skin has squamous cell hyperplasia, the blood vessels contain many inflammatory cells, and there are no skin-dependent glands.

Figure 7A:
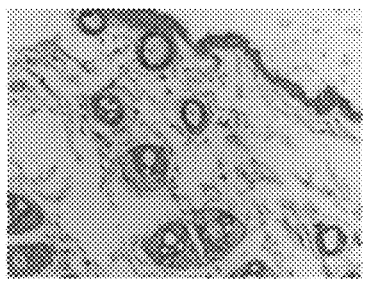
FIG. 7A is micromorphic image of the skin at the ulcer of Lot 1 (mice number 1)
Figure 7B:
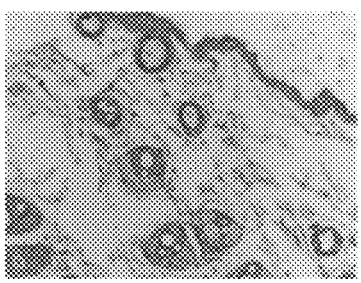
FIG. 7B is micromorphic image of the skin at the ulcer of Lot 1 (mice number 6)
Figure 7C:
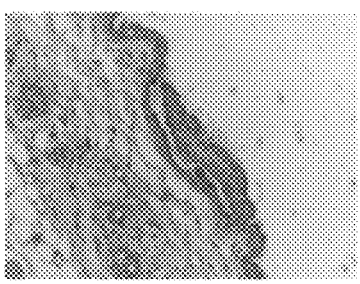
FIG. 7C is micromorphic image of the skin at the ulcer of Lot 1 (mice number 7)

Referring to FIG. 7A-7C, all of the micromorphic images of the skin at the ulcer has the following characteristics: normal skin structure; skin covered with stratified squamous epithelium has well-structured keratinization, well-structured basement membrane, well-structured skin appendages; and the stromal tissue has collagenous fibers, elastic fibers, and blood vessels.

Figure 7D:
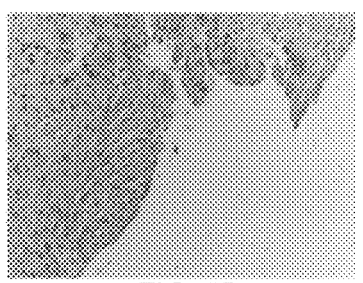
FIG. 7D is micromorphic image of skin at the ulcer of Lot 2 (mice number 13)

Referring to FIG. 7D is a micromorphic image of the skin at the ulcer has the following characteristics: the skin has many areas where the entire epidermis is lost, leaving only a fibrous band and clusters of inflammatory cells, no blood vessels.

Figure 7E:
FIG. 7E is micromorphic image of skin at the ulcer of Lot 2 (mice number 15)

Referring to FIG. 7E is a micromorphic image of the skin at the ulcer has the following characteristics: the skin has many areas where the entire epidermis is lost, leaving only a fibrous band and clusters of inflammatory cells, no blood vessels, there are many times keratinized area, some cells atrophy.

Figure 7F:
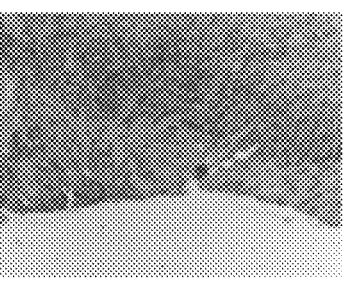
FIG. 7F is micromorphic image of skin at the ulcer of Lot 2 (mice number 19)

Referring to FIG. 7F is a micromorphic image of the skin at the ulcer has the following characteristics: the skin has deep ulcerated band without the epidermis, only inflammatory cells, white blood cells, no blood vessels.

Figure 7G:
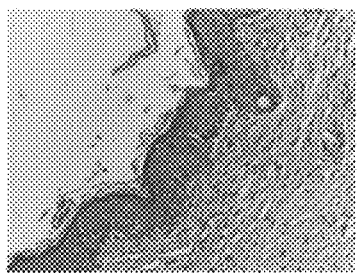
FIG. 7G is micromorphic image of skin at the ulcer of Lot 4 (mice number 21)

Referring to FIG. 7G is a micromorphic image of the skin at the ulcer has the following characteristics: the skin has a regeneration of few rows of epidermal cells, there is no formation of skin-dependent glands, few blood vessels.

Figure 7H:
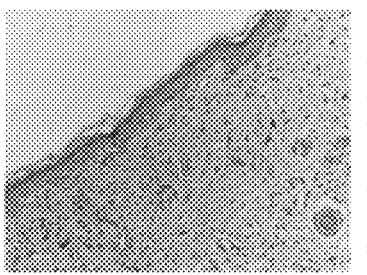
FIG. 7H is micromorphic image of skin at the ulcer of Lot 4 (mice number 19)

Referring to FIG. 7H is a micromorphic image of the skin at the ulcer has the following characteristics: skin has regeneration, but have only new epidermis contains many rows of cells, no skin-dependent glands.

Figure 7I:
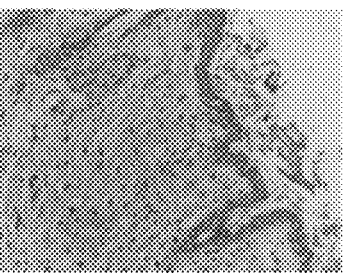
FIG. 7I is micromorphic image of skin at the ulcer of Lot 4 (mice number 29)

Referring to FIG. 7I is a micromorphic image of the skin at the ulcer has the following characteristics: the skin has regeneration of the epidermis, there is no formation of skin-dependent glands, few blood vessels, and sparse connective cells.

Figure 7J:
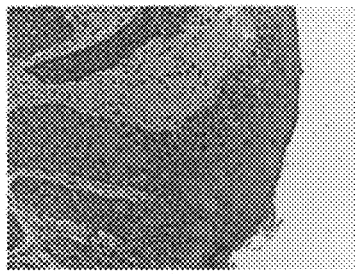
FIG. 7J is micromorphic image of skin at the ulcer of Lot 5 (mice number 33)

Referring to FIG. 7J is a micromorphic image of the skin at the ulcer has the following characteristics: the skin has squamous cell hyperplasia, causing the epidermis to deepen, and the connective tissue is sparse; less blood vessels, more horny, there is no formation of skin-dependent glands.

Figure 7K:
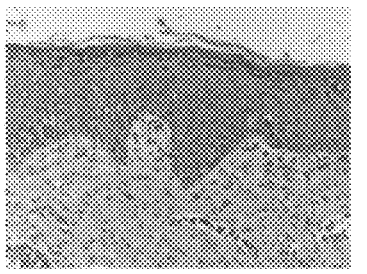
FIG. 7K is micromorphic image of skin at the ulcer of Lot 5 (mice number 35)

Referring to FIG. 7K is a micromorphic image of the skin at the ulcer has the following characteristics: the skin has hyperplasia of the squamous cell layer, the blood vessels have many inflammatory cells, and the cells are less connected.

Figure 7L:
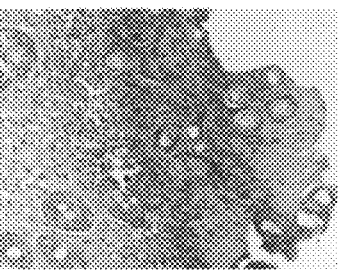
FIG. 7L is micromorphic image of skin at the ulcer of Lot 5 (mice number 37)

Referring to FIG. 7L is a micromorphic image of the skin at the ulcer has the following characteristics: the skin has uneven regeneration, there are areas of necrosis with many inflammatory cells.

Figure 7M:
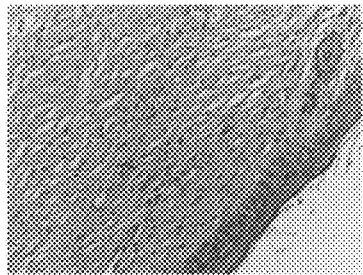
FIG. 7M is micromorphic image of skin at the ulcer of Lot 3 (mice number 46)

Referring to FIG. 7M is a micromorphic image of the skin at the ulcer has the following characteristics: skin has a polymorphic regeneration of the epidermis but not an entire layer, skin-dependent glands have not yet formed.

Figure 7N:
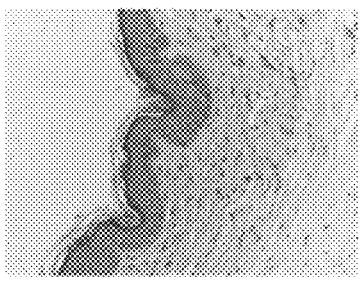
FIG. 7N is micromorphic image of skin at the ulcer of Lot 3 (mice number 48)

Referring to FIG. 7N is a micromorphic image of the skin at the ulcer has the following characteristics: the skin has a polymorphic regeneration of the epidermis but the layers have very few cells, no skin-dependent glands, few blood vessels and few epidermal cells.

Figure 7O:
FIG. 7O is micromorphic image of skin at the ulcer of Lot 3 (mice number 49)

Referring to FIG. 7O is a micromorphic image of the skin at the ulcer has the following characteristics: the skin has regenerated to form the epidermis but the cell lines are few, the skin-dependent glands are not present, the blood vessels are few, nucleated connective cells.

Results experiment of evaluation of the systemic effects of composition 100 and composition 200 on experimentally induced skin ulcers in white mice, including: (A1') General condition and body weight change of rats; (A2') Evaluation of hematopoietic function, (A3') Assess the extent of liver cell damage; (A4') Assessment of liver function, (A5') Assess kidney function, and (A6') Histopathological changes (macroscopic, microscopic).

(A1) General condition and body weight change of mice: During the experiment, mice in Lot 1, Lot 4, and Lot 5 were active, agile, bright eyes, and dry stools. No special expression was observed in all said 3 Lots of mice during the study period. Results effect of composition 100 and composition 200 on mice body weight listed in Table 19 below. After 21 days of applying the composition 100/composition 200, the weight of mice in the Lot 1 increased compared to before the study, the difference was statistically significant (p<0.05). There was no difference in the degree of change in mice weight between Lot 1, Lot 4, and Lot 5 (p>0.05).

TABLE 19

Effect of the composition 100 and the composition 200 on mice body weight.

| Mice lot | Weight (gam) | | $P_{before-after}$ |
|---|---|---|---|
| | Before research | After 21 days | |
| Lot 1 | 33.60 ± 1.17 | 40.70 ± 2.58 | <0.05 |
| Lot 4 | 33.10 ± 2.02 | 38.90 ± 3.73 | <0.05 |
| p compare to Lot 1 | >0.05 | >0.05 | |
| Lot 5 | 32.50 ± 1.96 | 40.50 ± 3.24 | <0.05 |
| p compare to Lot 1 | >0.05 | >0.05 | |

(A2')-(A5') based on standards including: red blood cell count, hemoglobin content, hematocrit content, mean erythrocyte volume, white blood cell count, white blood cell formula, platelet count, AST activity, ALT activity, total bilirubin concentration, albumin concentration, total cholesterol concentration, and creatinine concentration. All said standards of Lot 4 and Lot 5 had no statistically significant difference compared with Lot 1 and compared between at times before and after applying the composition 100/composition 200 ($p > 0.05$) (referenced by Table 20-25 below).

TABLE 20

Effect of the composition 100 and the composition 200 on red blood cell count, hemoglobin content count, hematocrit count, mean erythrocyte volume in the blood of mice.

| Mice lot | Red blood cell counts (T/I) | Hemoglobin content (g/dl) | Hematocrit (%) | Mean erythrocyte volume (fl) |
|---|---|---|---|---|
| Lot 1 | 8.95 ± 1.55 | 9.50 ± 1.66 | 43.05 ± 5.35 | 46.40 ± 2.32 |
| Lot 4 | 8.74 ±1.28 | 9.09 ± 1.43 | 40.31 ± 5.13 | 46.00 ± 2.21 |
| p compare to Lot 1 | >0.05 | >0.05 | >0.05 | >0.05 |
| Lot 5 | 8.43 ± 1.08 | 9.54 ± 1.15 | 41.67 ± 4.70 | 48.10 ± 2.18 |
| p compare to Lot 1 | >0.05 | >0.05 | >0.05 | >0.05 |

TABLE 21

Effect of the composition 100 and the composition 200 on white blood cell count, and white blood cell formula in the blood of mice.

| Mice lot | white blood cell count (G/I) | lymphocytes (%) | Neutrophil (%) |
|---|---|---|---|
| Lot 1 | 6.07 ± 1.58 | 69.81 ± 8.33 | 11.01 ± 3.40 |
| Lot 4 | 5.83 ± 1.05 | 65.35 ± 8.28 | 10.74 ± 3.33 |
| p compare to Lot 1 | >0.05 | >0.05 | >0.05 |
| Lot 5 | 5.04 ± 1.31 | 65.69 ± 3.97 | 11.52 ± 2.90 |
| p compare to Lot 1 | >0.05 | >0.05 | >0.05 |

TABLE 22

Effect of the composition 100 and the composition 200 on platelet count in the blood of mice.

| Mice lot | Platelet count (G/l) |
|---|---|
| Lot 1 | 821.20 ± 88.15 |
| Lot 4 | 861.70 ± 92.80 |
| p compare to Lot 1 | >0.05 |
| Lot 5 | 850.10 ± 80.55 |
| p compare to Lot 1 | >0.05 |

TABLE 23

Effect of the composition 100 and the composition 200 on AST activity, and ALT activity in the blood of mice.

| Mice lot | AST activity (UI/l) | ALT activity (UI/l) |
|---|---|---|
| Lot 1 | 129.50 ± 19.33 | 80.80 ± 12.01 |
| Lot 4 | 135.60 ± 18.43 | 86.50 ± 17.16 |
| p compare to Lot 1 | >0.05 | >0.05 |
| Lot 5 | 131.70 ± 23.88 | 76.50 ± 13.19 |
| p compare to Lot 1 | >0.05 | >0.05 |

TABLE 24

Effect of the composition 100 and the composition 200 on the total bilirubin concentration, albumin concentration, and total cholesterol concentration in the blood of mice.

| Mice lot | Total bilirubin concentration (mmol/l) | Albumin concentration (g/dl) | Total cholesterol concentration (mmol/l) |
|---|---|---|---|
| Lot 1 | 9.65 ± 0.65 | 2.95 ± 0.35 | 2.27 ± 0.34 |
| Lot 4 | 10.17 ± 0.92 | 3.23 ± 0.33 | 2.18 ± 0.25 |
| p compare to Lot 1 | >0.05 | >0.05 | >0.05 |
| Lot 5 | 9.85 ± 0.82 | 3.14 ± 0.30 | 2.02 ± 0.19 |
| p compare to Lot 1 | >0.05 | >0.05 | >0.05 |

TABLE 25

Effect of the composition 100 and the composition 200 on the creatinine concentration.

| Mice lot | Creatinine concentration (mg/dl) |
|---|---|
| Lot 1 | 0.82 ± 0.15 |
| Lot 4 | 0.79 ± 0.17 |
| p compare to Lot 1 | >0.05 |
| Lot 5 | 0.78 ± 0.18 |
| p compare to Lot 1 | >0.05 |

(A6') Histopathological changes based on standards related to macroscopicand and microstructure of liver and kidney of mice. For macroscopic: in all experimental rats (both Lot 1, Lot 4, and Lot 5) do not gross pathological changes were observed in the heart, lung, liver, spleen, pancreas, kidney and gastrointestinal organs of mice.

Figure 8A:
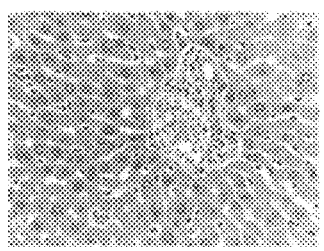
FIG. 8A is a microscopic image of the liver of the mice Lot 1 (Rat number 01) (HE×400-Hematoxylin—Eosin staining, 400× magnification), normal liver.
Figure 8B:
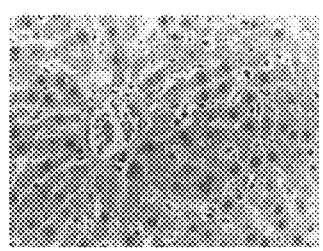
FIG. 8B is a microscopic image of the liver of the mice Lot 1 (Rat number 06) (HE×400), normal liver.
Figure 8C:
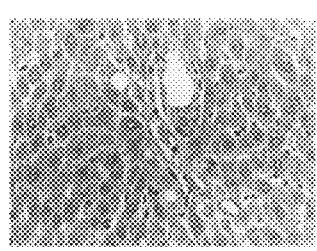
FIG. 8C is a microscopic image of the liver of the mice Lot 1 (Rat number 07) (HE×400), normal liver.
Figure 8D:
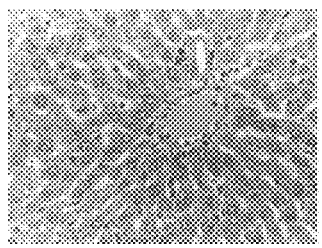
FIG. 8D is a microscopic image of the liver of the mice Lot 4 (Rat number 21) (HE×400), normal liver.
Figure 8E:
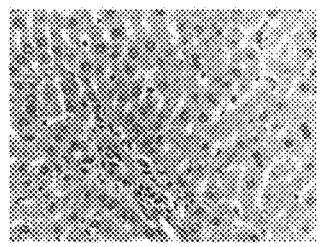
FIG. 8E is a microscopic image of the liver of the mice Lot 4 (Rat number 23) (HE×400), normal liver.
Figure 8F:
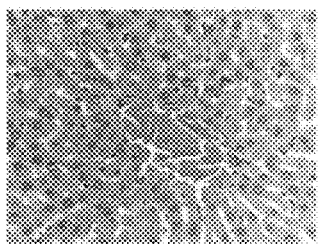
FIG. 8F is a microscopic image of the liver of the mice Lot 4 (Rat number 29) (HE×400), normal liver.
Figure 8G:
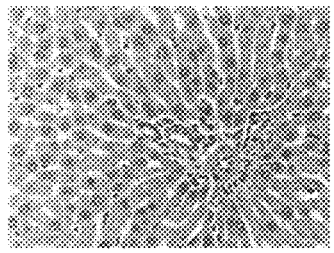
FIG. 8G is a microscopic image of the liver of the mice Lot 5 (Rat number 33) (HE×400), normal liver.
Figure 8H:
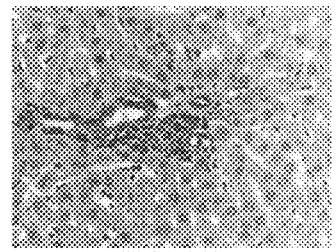
FIG. 8H is a microscopic image of the liver of the mice Lot 5 (Rat number 35) (HE×400), normal liver.
Figure 8I:
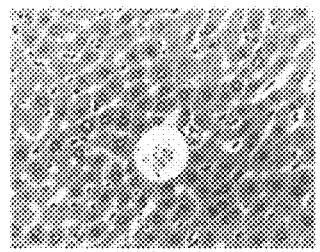
FIG. 8I is a microscopic image of the liver of the mice Lot 5 (Rat number 37) (HE×400), normal liver.
Figure 8J:
FIG. 8J is a microscopic image of the kidney of the mice Lot 1 (Rat number 01) (HE×400-Hematoxylin—Eosin staining, 400× magnification), normal kidney.
Figure 8K:
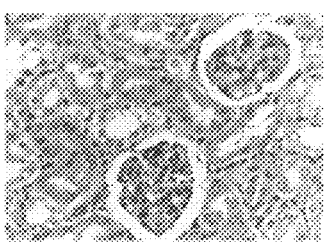
FIG. 8K is a microscopic image of the kidney of the mice Lot 1 (Rat number 06) (HE×400), normal kidney.
Figure 8L:
FIG. 8L is a microscopic image of the kidney of the mice Lot 1 (Rat number 07) (HE×400), normal kidney.
Figure 8M:
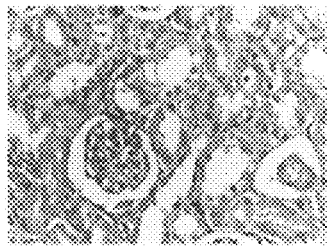
FIG. 8M is a microscopic image of the kidney of the mice Lot 4 (Rat number 21) (HE×400), normal kidney.
Figure 8N:
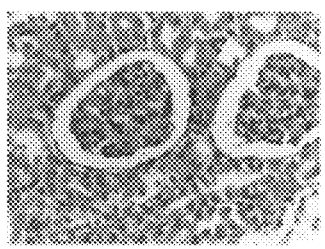
FIG. 8N is a microscopic image of the kidney of the mice Lot 4 (Rat number 23) (HE×400), normal kidney.
Figure 8O:
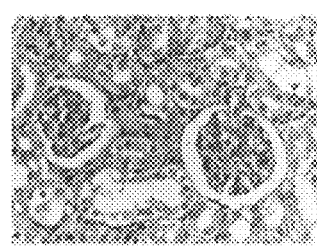
FIG. 8O is a microscopic image of the kidney of the mice Lot 4 (Rat number 29) (HE×400), normal kidney.
Figure 8P:
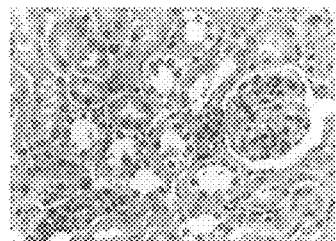
FIG. 8P is a microscopic image of the kidney of the mice Lot 5 (Rat number 33) (HE×400), normal kidney.
Figure 8Q:
FIG. 8Q is a microscopic image of the kidney of the mice Lot 5 (Rat number 35) (HE×400), normal kidney.
Figure 8R:
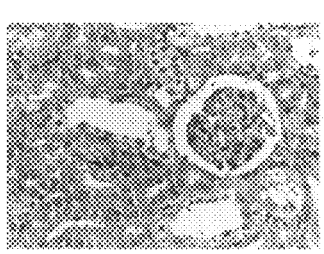
FIG. 8R is a microscopic image of the kidney of the mice Lot 5 (Rat number 37) (HE×400), normal kidney.

Result microscopic images of the mice liver of Lot 1, Lot 4, and Lot 5 referenced from FIG. 8A to FIG. 8R, showed that the hepatocytes and renal cells were functioning normally.

Summary Results of Scar Treatment:

Scar treatment effects of the composition 100 and composition 200 applied at a dose of 0.3 ml/ulcer/time, 2 times/day had the effect of treating experimental scar shown by reducing the ulcer area, increasing the concentration of hydroxyprolin in the skin compared with the Lot 2 after 21 days of applied; wherein skin micrographs show that the mice skin of the Lot 4 and Lot 5 have improved markedly compared to the Lot 2 at the same time; and Systemic effects of coposition 100 and composition 200 applied externally skin in white mice injured by doxorubicin:

Both the compositions did not affect the general condition, the level of weight gain of rat compared with the Lot 1;
  Does not change the results of tests to evaluate hematopoietic function (red blood cell count, hemoglobin content, hematocrit, mean red blood cell volume, white blood cell count, white blood cell count, platelet count, and platelet count) compared with the Lot 1;
  Did not change the results of liver function tests (concentrations of total bilirubin, albumin and total cholesterol in the blood of mice) compared with the Lot 1;
  No damage to liver cells (AST, ALT activity in rat blood) compared with the Lot 1;
  Does not change the test results of creatinine in the blood of mice after 21 days of continuous said composition use with the Lot 1;
  There was no morphological damage when observing the macroscopic organs of mice compared with the Lot 1; and Microstructure of liver and kidney of mice: There was no significant difference compared with the Lot 1 after 21 days of continuous reagent use.

From the results of the investigation of burn and scar healing properties mentioned above, it is found the composition 100 and composition 200 of the present invention that is used at a dose of 0.05-0.1 mL/cm2 of skin, with a frequency of twice daily, had increased effect of scar healing in experimental doxorubicin-induced rat/mice models of skin ulceration, increased concentration of hydroxyprolin in skin, improved skin microstructure compared to control models after 21 days of application; and had no systemic toxicity after 21 days of application in the doxorubicin-induced skin ulcered rat/mice.

The composition 100 and composition 200 according to the embodiment of the invention are also examined for physicochemical properties. Specifically, the samples were analyzed at the National Institute for Food Control (NIFC), the results are listed in Table 26 below.

TABLE 26

Results of physicochemical properties of the composition 100 and composition 200.

| No. | Quality criteria | | Unit | Test method | Result |
|---|---|---|---|---|---|
| 1 | Clostridium perfringens | | CFU/g | TCVN 4991:2005 | KPH (LOD:1) |
| 2 | Coliforms | | CFU/g | TCVN 6848:2007 | KPH (LOD:1) |
| 3 | Escherichia coli | | CFU/g | TCVN 7924-2:2008 | KPH (LOD:1) |
| 4 | Total of yeast and mold count | | CFU/g | TCVN 8275-2:2010 | KPH (LOD:1) |
| 5 | Total aerobic microorganisms | | CFU/g | TCVN 4884-1:2015 | KPH (LOD:1) |
| 6 | Cadmium | | mg/Kg | NIFC.03.M.45 (ICP-MS) | KPH (LOD:1) |
| 7 | Lead | | mg/Kg | NIFC.03.M.45 (ICP-MS) | 0.020 |
| 8 | Mercury | | mg/Kg | NIFC.03.M.45 (ICP-MS) | KPH (LOD: 0.004) |
| 9 | Curcumin | Composition 100 | mg/g | NIFC.05.M.132 (ICP-MS) | 3.26 |
|   |   | Composition 200 |   |   | 0.48 | wherein KPH means not detected (below the detection threshold of the limit of detection (LOD) test method).

Figure 9:
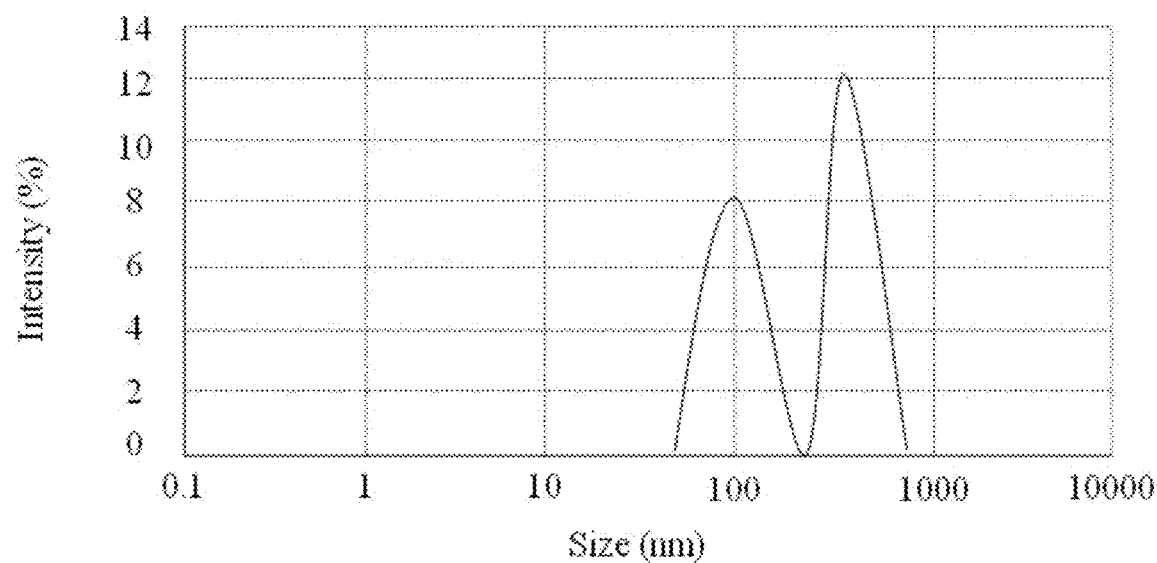
FIG. 9 is a flowchart showing the particle size distribution according to the intensity of composition 100.
Figure 10:
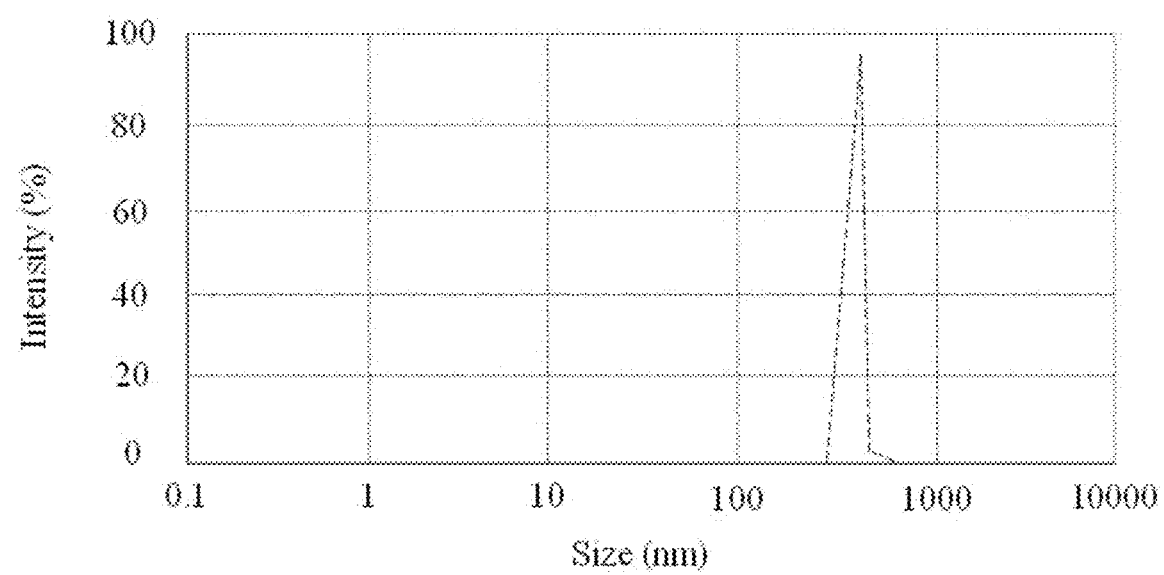
FIG. 10 is a flowchart showing the particle size distribution according to the intensity of composition 200.

References to FIG. 9-10 are charts showing the resulting particle sizes of composition 100 and composition 200 for the example of the present invention, that is 206 nm, and 344 nm, respectively. The compositions are stable, homogenous, and well dispersed in water when measuring, which proves that the solubility limitation has been overcome.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

The invention claimed is:

1. A method of manufacturing a nano liquid composition containing curcumin, wherein the composition has the ability to treat burns and increase the effect of scar healing, wherein the method comprises steps performed in the following specific order:
   (a) creating a curcumin nano ingredient comprising performing in a specific order from (i) to (v):
       (i) preparing a dispersed phase by dissolving 4 parts of a curcumin with 5 parts of ethanol;
       (ii) creating a carrier mixture by homogeneously dissolving 1.5 parts polyethylene glycol with 6 parts ethylene glycol and 2 parts water, with the combination of ultrasonic vibration for 2 hours at room temperature;
       (iii) creating a homogeneous mixture by dissolving 1.6 parts of the dispersed phase at step (i) with 1.5 parts of the carrier mixture at step (ii), and 2 parts lecithin, wherein the homogeneous mixture is created with emulsifying equipment;
       (iv) keeping the homogeneous mixture overnight; and
       (v) centrifuging said homogenized mixture at step (iv) with a speed of 5000 rpm for 10 min, wherein centrifugation is repeated 6 times to obtain the curcumin nano ingredient in the form of a microemulsion;

(b) creating a foundation mixture by homogenously mixing the following ingredients:
  a phosphatidylcholine having 15%-20% by weight;
  a cholesterol having 18%-25% by weight;
  a lecithin having 25%-30% by weight;
  a folic acid having 8%-12% by weight;
  the curcumin nano ingredient having 12%-20% by weight;
  a tocopherol having 2%-5% by weight;
  a xanthan gum having 2%-5% by weight;
  a *Camellia sinensis* extracts ingredient having 2%-5% by weight;
  and an aloe vera extracts ingredient having 0.25%-1% by weight;
(c) homogenously mixing the curcumin nano ingredient at step (a) with the foundation mixture at step (b) in a ratio of 1:1 for 2 hours at 120° C. with the emulsifying equipment to create a nano liquid composition containing curcumin, wherein the composition has the ability to treat burns and increase the effect of scar healing;
(d) applying the nano liquid composition to the skin of a subject in need thereof.

2. The method of claim 1, wherein the foundation mixture comprises:
  the phosphatidylcholine having 18% by weight;
  the cholesterol having 21% by weight;
  the lecithin having 27% by weight;
  the folic acid having 9.5% by weight;
  the curcumin nano ingredient having 15% by weight;
  the tocopherol having 3% by weight;
  the xanthan gum having 3% by weight;
  the *Camellia sinensis* extracts ingredient having 3% by weight; and
  the aloe vera extracts ingredient having 0.5% by weight.

3. The method of claim 1, wherein at step (c) the nano liquid composition is used at a dose of 0.05-0.1 mL/cm$^2$ of skin, with a frequency of twice daily, to reduce the area of the burns, and to increase the concentration of hydroxyproline in the skin.

* * * * *